(12) United States Patent
Heaven et al.

(10) Patent No.: US 12,193,658 B2
(45) Date of Patent: Jan. 14, 2025

(54) DUAL EXPANSION ANCHOR

(71) Applicant: Conmed Corporation, Utica, NY (US)

(72) Inventors: Malcolm Heaven, Reno, NV (US); John P. Greelis, Carlsbad, CA (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 18/363,300

(22) Filed: Aug. 1, 2023

(65) Prior Publication Data

US 2024/0122591 A1 Apr. 18, 2024

Related U.S. Application Data

(60) Continuation of application No. 17/507,981, filed on Oct. 22, 2021, now Pat. No. 11,712,236, which is a (Continued)

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0409* (2013.01); *A61B 2017/0432* (2013.01); *A61B 2017/0438* (2013.01); *A61B 2017/0445* (2013.01); *A61B 2017/0456* (2013.01); *A61F 2002/0823* (2013.01)

(58) Field of Classification Search
CPC ........ A61B 17/0401; A61B 2017/0409; A61B 2017/042; A61B 2017/0422; A61B 2017/0424; A61B 2017/0429; A61B 2017/043; A61B 2017/0432; A61B 2017/0433; A61B 2017/0438; A61B 2017/0445; A61B 2017/0456; A61F 2/0811; A61F 2002/0817; A61F 2002/0823; A61F 2002/0835; A61F 2002/0876; A61F 2002/0882; A61F 2002/0888

See application file for complete search history.

(56) References Cited

U.S. PATENT DOCUMENTS 4,790,304 A * 12/1988 Rosenberg ......... A61B 17/7266
606/302
5,268,001 A * 12/1993 Nicholson ............. A61F 2/0811
606/232

(Continued)

*Primary Examiner* — Ryan J. Severson
(74) *Attorney, Agent, or Firm* — Bond, Schoeneck & King, PLLC; Frederick J. M. Price

(57) ABSTRACT

A bone anchor, including: a bone engaging member including: a first proximal bone engaging portion and a second distal bone engaging portion; and an expansion feature configured to allow radial expansion of the first bone engaging portion and the second bone engaging portion; an expander having a first proximal expansion portion and a second distal expansion portion and displaceable between a first position relative to the bone engaging member and a second position relative to the bone engaging member; a tissue capture feature; and wherein the first expansion portion of the expander is configured to expand the first bone engaging portion of the bone engaging member and the second expansion portion of the expander is configured to expand the second bone engaging portion of the bone engaging member when the expander is in the second position.

6 Claims, 30 Drawing Sheets

Related U.S. Application Data division of application No. 15/468,372, filed on Mar. 24, 2017, now Pat. No. 11,154,290, which is a division of application No. 14/349,654, filed as application No. PCT/US2012/058786 on Oct. 4, 2012, now Pat. No. 9,775,597.

(60) Provisional application No. 61/543,284, filed on Oct. 4, 2011.

(56) References Cited

U.S. PATENT DOCUMENTS

| | | | | |
|---|---|---|---|---|
| 5,814,071 A * | 9/1998 | McDevitt | A61B 17/0401 | 606/232 |
| 7,713,285 B1 * | 5/2010 | Stone | A61F 2/0811 | 606/232 |
| 8,221,479 B2 * | 7/2012 | Glazer | A61B 17/686 | 411/63 |
| 8,414,647 B2 * | 4/2013 | Baird | A61F 2/0811 | 623/13.12 |
| 8,523,902 B2 * | 9/2013 | Heaven | A61B 17/0401 | 606/232 |
| 8,545,535 B2 * | 10/2013 | Hirotsuka | A61B 17/0401 | 606/232 |
| 8,652,208 B2 * | 2/2014 | Baird | A61F 2/0811 | 623/13.12 |
| 8,906,060 B2 * | 12/2014 | Hart | A61B 17/0401 | 606/232 |
| 8,986,345 B2 * | 3/2015 | Denham | A61B 17/0401 | 606/232 |
| 9,044,313 B2 * | 6/2015 | Heaven | A61B 17/0401 | |
| 9,155,574 B2 * | 10/2015 | Saravia | A61B 17/1725 | |
| 9,706,984 B2 * | 7/2017 | Heaven | A61B 17/0401 | |
| 9,775,597 B2 * | 10/2017 | Heaven | A61B 17/0401 | |
| 9,826,970 B2 * | 11/2017 | Heaven | A61B 17/0401 | |
| 9,925,036 B2 * | 3/2018 | Heaven | A61B 17/0401 | |
| 9,968,349 B2 * | 5/2018 | Heaven | A61F 2/0811 | |
| 11,154,290 B2 * | 10/2021 | Heaven | A61B 17/0401 | |
| 11,712,236 B2 * | 8/2023 | Heaven | A61F 2/0811 | 606/232 |
| 2006/0235413 A1 * | 10/2006 | Denham | A61B 17/0401 | 606/907 |
| 2008/0183220 A1 * | 7/2008 | Glazer | A61B 17/686 | 606/301 |
| 2009/0043342 A1 * | 2/2009 | Freedland | A61F 2/3662 | 606/301 |
| 2010/0185283 A1 * | 7/2010 | Baird | A61F 2/0811 | 623/13.14 |
| 2010/0198258 A1 * | 8/2010 | Heaven | A61B 17/0401 | 606/232 |
| 2010/0292732 A1 * | 11/2010 | Hirotsuka | B29C 45/00 | 606/232 |
| 2010/0331881 A1 * | 12/2010 | Hart | A61B 17/0401 | 606/232 |
| 2011/0112550 A1 * | 5/2011 | Heaven | A61B 17/0401 | 606/151 |
| 2011/0184516 A1 * | 7/2011 | Baird | A61B 17/86 | 623/13.14 |
| 2012/0239038 A1 * | 9/2012 | Saravia | A61B 17/7266 | 606/64 |
| 2013/0338710 A1 * | 12/2013 | Heaven | A61B 17/0401 | 606/232 |
| 2014/0046369 A1 * | 2/2014 | Heaven | A61F 2/0811 | 606/232 |
| 2014/0249579 A1 * | 9/2014 | Heaven | A61F 2/0811 | 606/232 |
| 2016/0038274 A1 * | 2/2016 | Heaven | A61B 17/0401 | 623/13.12 |
| 2017/0189010 A1 * | 7/2017 | Heaven | A61B 17/0401 | |
| 2017/0265854 A1 * | 9/2017 | Heaven | A61B 17/0401 | |
| 2018/0125473 A1 * | 5/2018 | Heaven | A61B 17/0401 | |
| 2018/0161147 A1 * | 6/2018 | Heaven | A61F 2/0811 | |
| 2018/0333153 A1 * | 11/2018 | Heaven | A61F 2/0811 | |
| 2022/0039792 A1 * | 2/2022 | Heaven | A61F 2/0811 | |

* cited by examiner

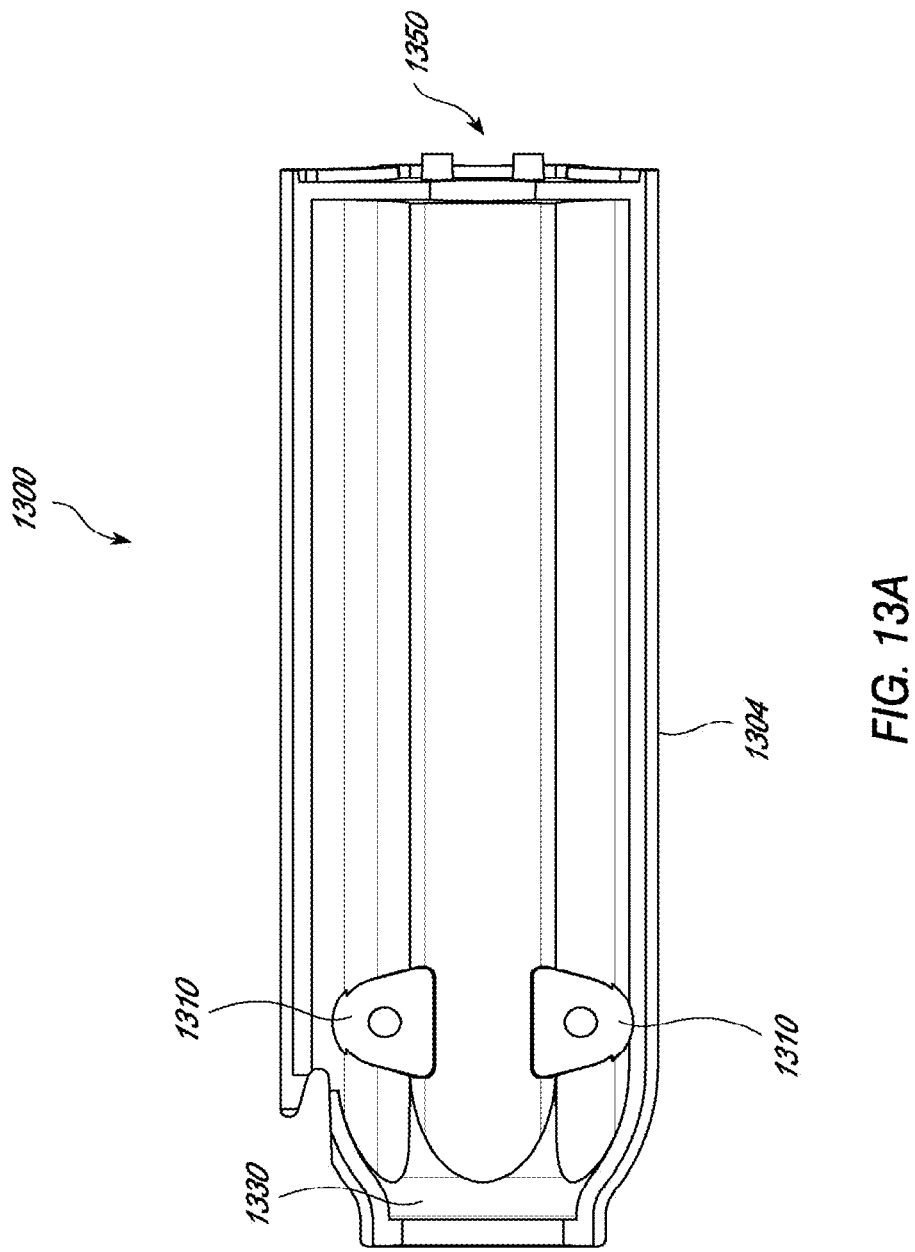

DUAL EXPANSION ANCHOR

CROSS-REFERENCE TO RELATED APPLICATIONS

This application is a continuation of U.S. patent application Ser. No. 17/507,981 (now U.S. Pat. No. 11,712,236) which is a divisional of U.S. patent application Ser. No. 15/468,372 filed on Mar. 24, 2017 (now U.S. Pat. No. 11,154,290) which is a divisional of, and claims priority to and the benefit of, U.S. patent application Ser. No. 14/349,654, filed on Apr. 3, 2014 (now U.S. Pat. No. 9,775,597), which is a National Phase Application pursuant to 35 U.S.C. 371 of International App. No. PCT/US12/58786, filed on Oct. 4, 2012, which claims priority to and the benefit of U.S. Prov. App. No. 61/543,284, filed on Oct. 4, 2011, the disclosures of each are relied upon and hereby incorporated by reference in their respective entireties.

BACKGROUND OF THE INVENTION

Field of the Invention

The present invention relates to medical devices and procedures. More particularly, the present invention relates to devices and methods for securing soft tissue to a rigid material such as bone.

Description of the Related Art

There are several medical procedures where a surgeon needs to attach soft tissue such as tendons or other soft connective tissue to bone. One common example is a biceps tenodesis, a surgical procedure usually performed for the treatment of biceps tendonitis of the shoulder. A biceps tenodesis may be performed as an isolated procedure, but more often is part of a larger shoulder surgery such as a rotator cuff repair.

The biceps tendon connects the biceps muscle to the bone. The tendon passes from the muscle to the shoulder joint. Patients with biceps tendon problems may have a detachment of the biceps tendon from the radial tuberosity, for example, or they may have inflammation and irritation of the biceps tendon itself. Biceps tendon problems can also occur in conjunction with a rotator cuff tear.

A biceps tenodesis is a procedure that cuts the normal attachment of the biceps tendon on the shoulder socket and reattaches the tendon to the bone of the humerus (arm bone). By performing a biceps tenodesis, the pressure of the biceps attachment is taken off the cartilage rim of the shoulder socket (the labrum), and a portion of the biceps tendon can be surgically removed. Essentially a biceps tenodesis moves the attachment of the biceps tendon to a position that is out of the way of the shoulder joint.

To perform a biceps tenodesis repair, typically a surgical procedure is used and requires the multiple steps of externalizing the tendon, whip stitching it, threading suture through a tenodesis screw, drilling the necessary bone hole and anchor insertion via screwing it in. This is a difficult procedure arthroscopically. Systems recently brought to market still require multiple steps and tools

SUMMARY OF THE INVENTION

Some embodiments relate to a bone anchor. A bone anchor can include, for example, a bone engaging member having a first proximal bone engaging portion and a second distal bone engaging portion and an expansion feature that allows radial expansion of the first bone engaging portion and the second bone engaging portion. A bone anchor can further include an expander with a first proximal expansion portion and a second distal expansion portion and displaceable between a first position relative to the bone engaging member and a second position relative to the bone engaging member and a tissue capture feature. In some embodiments, the first expansion portion of the expander can expand the first bone engaging portion of the bone engaging member and the second expansion portion of the expander can expand the second bone engaging portion of the bone engaging member when the expander is in the second position.

Some embodiments relate to a bone anchor. A bone anchor can include, for example, a bone engaging member having a first end and a second end. The bone engaging member can include a first plurality of bone-engaging tines extending longitudinally towards the first end, a second plurality of bone-engaging tines extending longitudinally towards the second end, and an expander having a first portion and a second portion positioned along a longitudinal axis. In some embodiments, the expander can be positioned between the first plurality of bone engaging tines when the expander is in a first position. In some embodiments, the expander is positioned between the first plurality of bone engaging tines and between the second plurality of bone engaging tines when the expander is in a second position. In some embodiments, the expander can expand both the first set of tines and the second set of tines outward upon movement of the expander relative to the bone-engaging member from a first position to a second position.

Some embodiments relate to a bone anchor. A bone anchor can include, for example, a bone engaging member having a first proximal bone engaging portion and a second distal bone engaging portion and an expansion feature that allows radial expansion of the first bone engaging portion and the second bone engaging portion. Some embodiments of a bone anchor can include a two piece expander having a first expansion member with a first expansion portion and a second expansion member with a second expansion portion. In some embodiments, the first expansion member and the second expansion member can be displaceable between first positions relative to the bone engaging member and second positions relative to the bone engaging member. Some embodiments of a bone anchor can include a tissue capture feature. In some embodiments of a bone anchor, the first expansion portion of the first expansion member can expand the first bone engaging portion of the bone engaging member and the second expansion portion of the second expansion member can expand the second bone engaging portion of the bone engaging member when first and second expansion members are in their second positions.

Some embodiments relate to a method of attaching soft tissue to bone. The method can include, for example, inserting tissue and an anchor having a first expandable bone engaging portion at a first end of the anchor and a second expandable bone engaging portion at a second end of the anchor into the bone, expanding the first expandable bone engaging portion of the anchor to engage the bone, and expanding the second expandable bone engaging portion of the anchor to engage the bone.

BRIEF DESCRIPTION OF THE DRAWINGS

FIG. 13A is a side view of one embodiment of a portion of a handle body.

DETAILED DESCRIPTION OF THE PREFERRED EMBODIMENT

Figure 1:
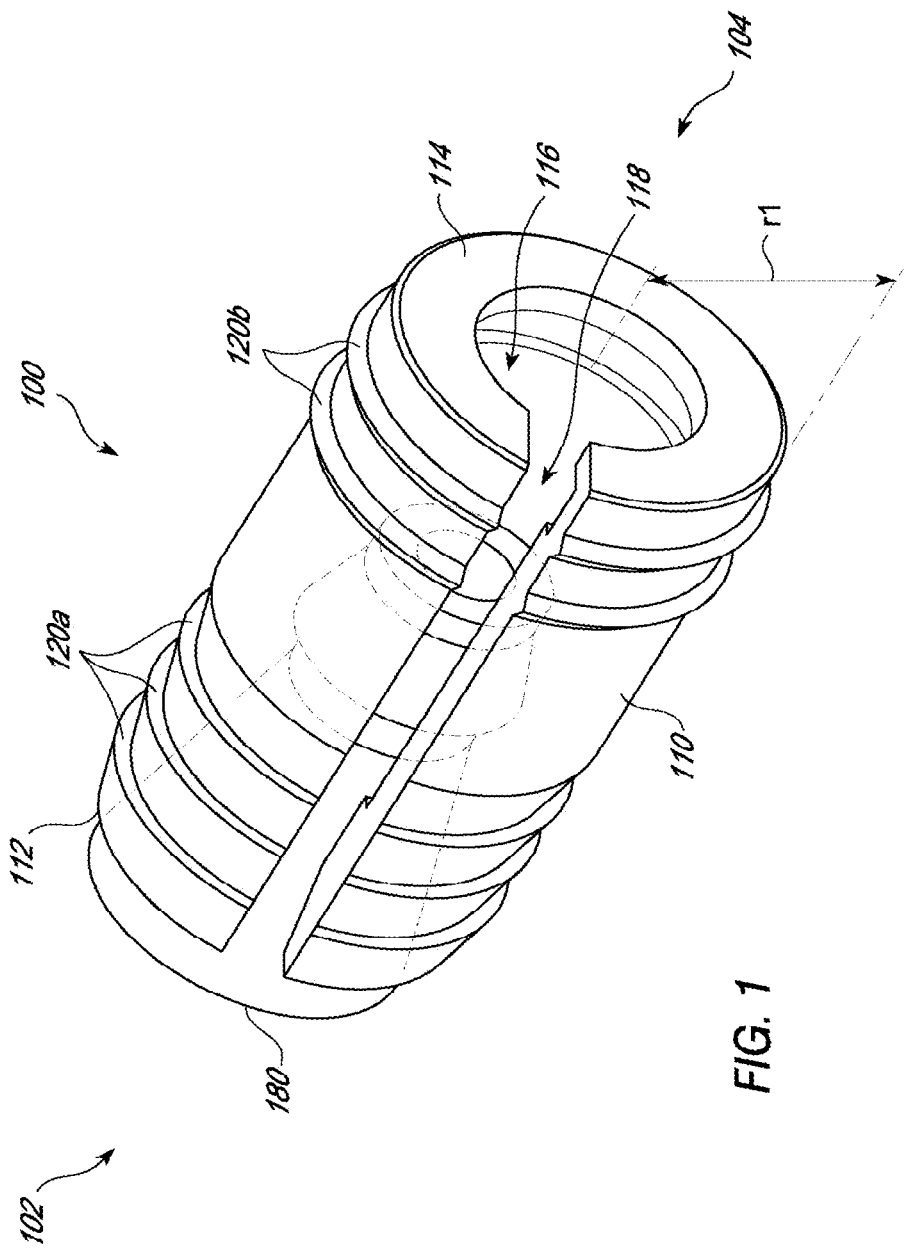
FIG. 1 depicts a perspective view of one embodiment of a split dual expansion anchor in an undeployed or unexpanded state.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Some embodiments disclosed herein relate generally to anchors for use in anchoring tissue or objects in a body. More specifically, some embodiments disclosed herein relate generally to anchors for use in anchoring soft tissue to bone in a body. Some embodiments disclosed herein relate generally to anchors for use in anchoring sutures to a bone in a body. Also some elements relate to individual components and subcomponents of the systems described herein, as well as methods of making and using the same. Some embodiments additionally relate to kits and components used in connection with the anchor. Although the following embodiments refer to the use of an anchor in anchoring tissue, a person of skill in the art will recognize that an anchor can be used to anchor any range of items within a body.

An exemplary dual expansion anchor can include features configured for retention of the desired tissue and features configured for affixing the anchor to the desired anchor point. FIG. 1 depicts a perspective view of one embodiment of an unexpanded dual expansion anchor 100 comprising an anchor body 110 and an expander 180. An anchor has a distal end 102 and a proximal end 104. The anchor 100 depicted in FIG. 1 has a radius of r1. An anchor can have a variety of dimensions. In some embodiments, for example, an anchor can have a length of 5 mm, 10 mm, 17 mm, 20 mm, 30 mm, 50 mm, or any other desired length. In some embodiments, for example, an anchor can have a diameter of 1 mm, 5 mm, 6 mm, 10 mm, 20 mm, or any other desired diameter.

The anchor body 110 has a first end 112 and a second end 114. In some embodiments, the first end 112 of the anchor body 110 is configured for placement into an anchor location. In some embodiments, the first end 112 of the anchor body 110 is configured for placement into a hole in a bone. In some embodiments, the second end 114 of the anchor body 110 is likewise configured for placement into an anchor location, or into a hole in a bone. In some embodiments, the anchor 100 is placed in the hole in the bone so that the second end 114 is in closer proximity to the entrance hole into the bone than the first end 112.

An anchor 100 can be inserted into an anchor point with an insertion tool. In some embodiments, the second end 114 of the anchor body 110 is configured for interaction with a portion of the insertion tool to thereby allow placement of the anchor 100 at the anchor point. In some embodiments, the second end 114 of the anchor body 110 can be configured to abut portions of the insertion tool. The abutting interaction between the anchor body 110 and the insertion tool can facilitate a transfer of forces between the insertion tool and the anchor body 114, which transfer of forces can facilitate anchor insertion and/or result in deployment or expansion of the anchor 100.

The anchor body 110 depicted in FIG. 1 has an axial bore 116. The axial bore 116 can extend partially or entirely through the anchor body 110. In some embodiments, the axial bore 116 can be a first axial bore partially extending along the length of the anchor body 110 and a second axial bore partially extending along the length of the anchor body 110. The axial bore 116 depicted in FIG. 1 extends the entire length of the anchor body 110.

The axial bore 116 can be sized and dimensioned to receive the expander 180. The expander 180 depicted in FIG. 1 is partially disposed within the axial bore 116 of the anchor body 110. The size and dimensions of the axial bore 116 will be discussed at greater length below.

The anchor body 110 depicted in FIG. 1 has an expansion slot 118 and teeth (or ridges) 120(*a*), 120(*b*). The expansion slot 118 allows the expansion of the anchor body 110 when the expander 180 is moved longitudinally in a direction from the first end 112 towards the second end 114. When the anchor 100 is placed within a hole in a bone, the longitudinal displacement of the expander 180 towards the second end 114 of the anchor body 110 results in the radial expansion of the anchor body 110. In some embodiments, the anchor body can be sized and dimensioned relative to the hole in which the anchor 100 is placed, so that the radial expansion of the anchor body resulting from the longitudinal displacement of the expander 180 towards the second end 114 causes the teeth 120(*a*), 120(*b*) to engage with bone surrounding the hole in which the anchor 100 is positioned. In some embodiments, the teeth 120(*a*), 120(*b*) are designed to prevent the anchor 100 from displacing out of the bone. In some embodiments, the teeth 120(*a*), 120(*b*) are designed to stabilize the anchor 100 in the bone. In some embodiments, the teeth 120(*a*), 120(*b*) are designed to hold the anchored tissue in proximity to the bone. In some embodiments, the teeth 120(*a*), 120(*b*) are designed to perform a combination of these and other functions.

In some embodiments, the teeth 120(*a*), 120(*b*) may penetrate the bone, the teeth 120(*a*), 120(*b*) may partially penetrate the bone, the teeth 120(*a*), 120(*b*) may form depressions in the bone, or the teeth 120(*a*), 120(*b*) may deform to fit to the bone.

In some embodiments, all of the teeth 120(*a*), 120(*b*) on the anchor body 110 are similarly sized and dimensioned. As depicted in FIG. 1, an anchor body 110 may also have two or more types of teeth 120(*a*), 120(*b*). Specifically, as depicted in FIG. 1, and anchor body may have a first set of teeth 120(*a*) located proximate to the first end 112 of the anchor body 110 and a second set of teeth 120(*b*) located proximate to the second end 114 of the anchor body 110.

As depicted in FIG. 1, teeth 120(*a*), 120(*b*) can have a range of sizes and shapes. A first set of teeth 120(*a*) can be sized and shaped to particularly resist movement in one direction. A first set of teeth 120(*a*), as depicted in FIG. 1, sized and shaped to particularly resist movement in one direction can be asymmetrical. A second set of teeth 120(*b*) can be sized and shaped to equally resist movement in all directions. A second set of teeth 120(*b*), sized and shaped to equally resist movement in all directions can be symmetrical.

Figure 2:
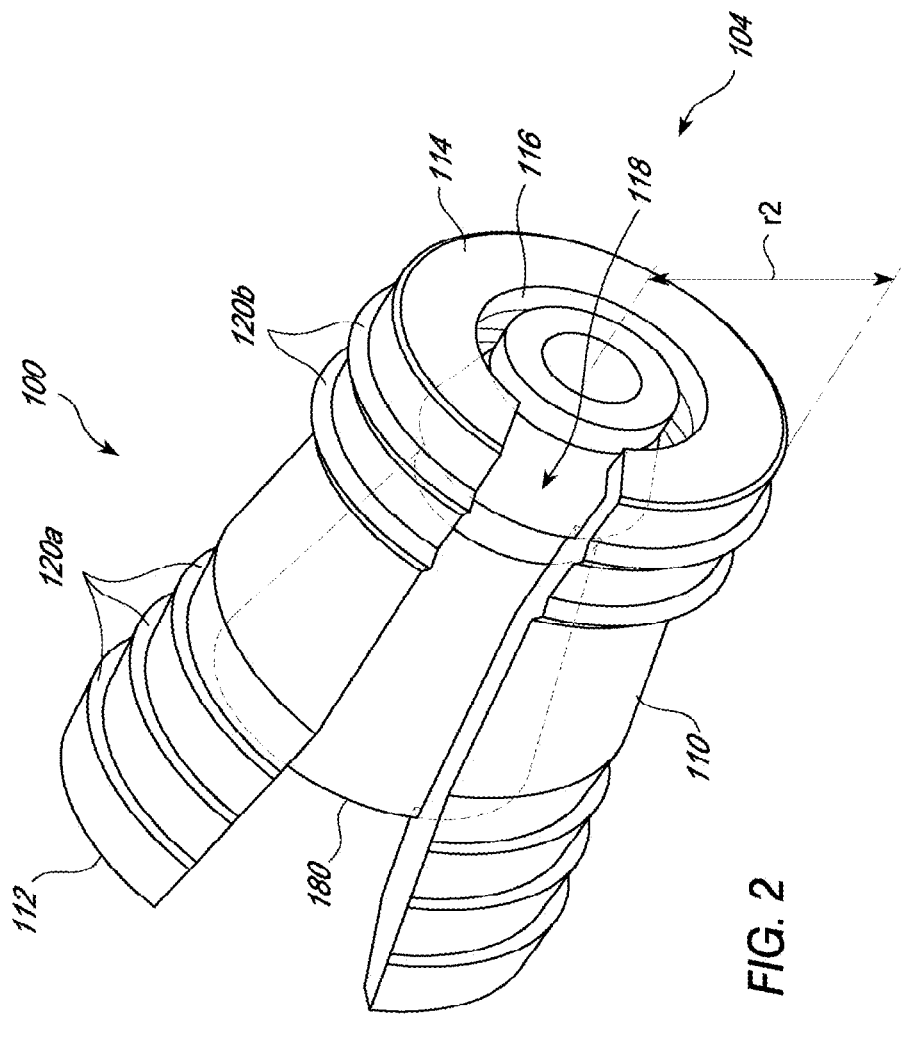
FIG. 2 depicts a perspective view of one embodiment of a split dual expansion anchor in a deployed or expanded state.

FIG. 2 depicts a perspective view of the same embodiment of the dual expansion anchor 100 comprising an anchor body 110 and an expander 180 depicted in FIG. 1. As also depicted in FIG. 1, the body 110 of the anchor 100 depicted in FIG. 2 has a first end 112, a second end 114, an axial bore 116, an expansion slot 118, and teeth 120(*a*), 120(*b*). As depicted in FIG. 2, the expander 180 is completely positioned within the axial bore 116 of the anchor body 110. With the expander 180 positioned completely within the axial bore 116 of the anchor body 110, the anchor 100 has a new radius r2. The expansion of the anchor body 110 caused by the new positioning of the expander 180 results in radius r2 being larger than radius r1 of the anchor 100 depicted in FIG. 1. Additionally, while FIG. 1 depicts an anchor 100 defined by a single radius r1, a person of skill in the art will recognize that a plurality of non-constant radii define some embodiments of an anchor 100. Thus, an expanded anchor 100 may have uniform or non-uniform radial expansion between a first end 112 and a second end 114.

The anchor 100 can have a variety of expanded dimensions. In some embodiments, for example, radius r2 is constant across the length of the anchor 100. In some embodiments, radius r2 varies across the length of the anchor 100. As depicted in FIG. 2, in some embodiments, radius r2 increases as the longitudinal distance to the first end 112 of the anchor 100 decreases.

Figure 3:
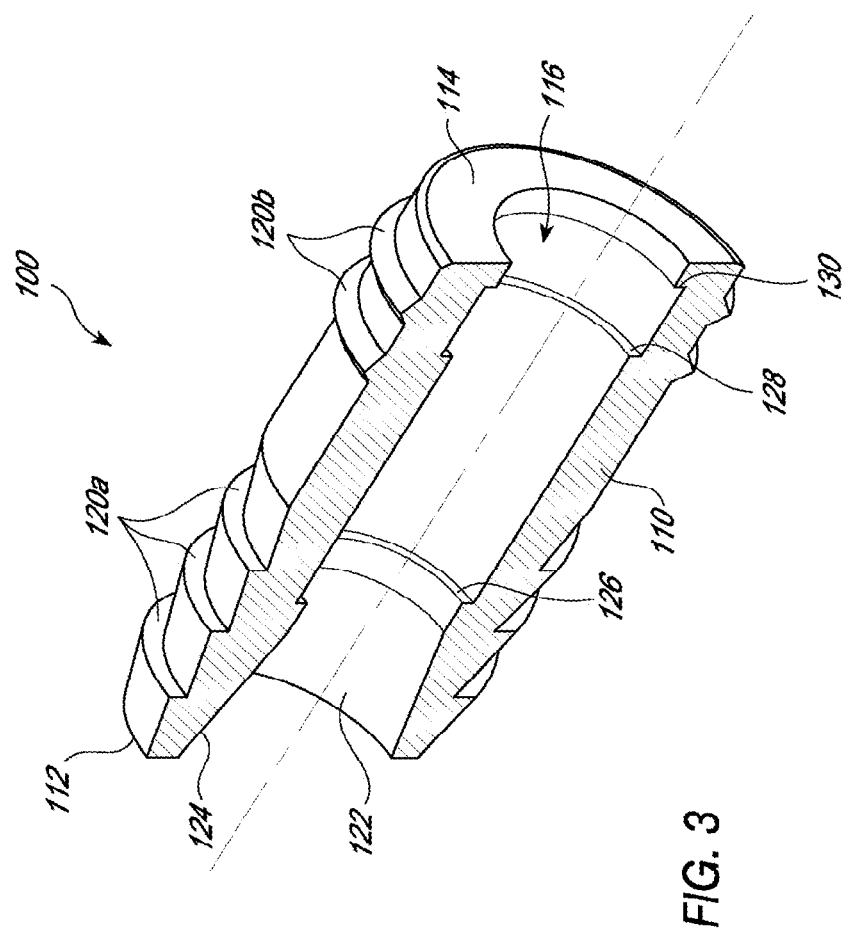
FIG. 3 depicts a cut-away view of one embodiment of a split dual expansion anchor in an undeployed or unexpanded state.

FIG. 3 depicts a perspective cut-away view of the same embodiment of the dual expansion anchor 100 comprising an anchor body 110. The body 110 of the anchor 100 depicted in FIG. 3 has a first end 112, a second end 114, an axial bore 116, an expansion slot (not shown), and teeth 120(*a*), 120(*b*). An axial bore 116 has a longitudinal axis 122 and can comprise a variety of shapes and sizes. In some embodiments, an axial bore may have a single shape and constant diameter throughout the length of the anchor body 110. In some embodiments, and as depicted in FIG. 3, the shape and size of the axial bore 116 may vary along the length of the anchor body 110. A person of skill in the art will recognize that variations in the shape and size of the axial bore 116 can be used in connection with variations in the size and shape of the expander (not shown) to achieve desired expansion of the anchor body 110, to achieve desired placement of the expander (not shown) within the anchor body 110, and to facilitate and/or prevent certain movements of the expander (not shown) within the anchor body 110.

As depicted in FIG. 3, and axial bore 116 can comprise portions that are parallel to the longitudinal axis 122 of the axial bore 116, perpendicular to the longitudinal axis 122 of the axial bore 116, or angled relative to the longitudinal axis 122 of the axial bore 116. The axial bore 116 can comprise a sloped portion 124. As depicted in FIG. 3, the sloped portion 124 can be located proximate to the first end 112 of the anchor body 110. The sloped portion 124 can be configured to provide a cam surface for the expander (not shown) to facilitate movement of the expander (not shown) into the axial bore 116 and to thereby facilitate increasing of the radius of the anchor body 110 from radius r1 to radius r2.

An axial bore 116 can include a first stop 126. As depicted in FIG. 3, a first stop 126 is a wall non-parallel, and in some embodiments, for example, perpendicular to the longitudinal axis 122 of the anchor body 110. As depicted in FIG. 3, the first stop 126 can be configured to provide an engageable surface to interact with portions of the expander (not shown) and thereby prevent the retraction of the expander (not shown) once the expander (not shown) has advanced past a designated point. Advantageously, prevention of the retraction of the expander (not shown) enables permanent placement of an anchor 100 in bone.

A first stop can be located a desired distance from the first end so as to achieve a desired degree of spreading of the first end 112 of the anchor body 110. In some embodiments, the first stop 126 can be located so that the first end 112 of the anchor body 110 achieves an expanded radius of approximately 40 millimeters, 20 millimeters, 10 millimeters, 5 millimeters, 2 millimeters, 1 millimeter, or any other desired diameter.

An axial bore 116 can include a second stop 128. As depicted in FIG. 3, a second stop 128 is a wall perpendicular to the longitudinal axis 122 of the anchor body 110. The second stop 128 can be configured to provide an engageable surface to interact with portions of the expander (not shown) and thereby prevent the retraction of the expander (not shown) once the expander (not shown) has advanced past a designated point. Advantageously, prevention of the retraction of the expander (not shown) enables the permanent placement of an anchor 100 in bone.

A second stop 128 can be located a desired distance from the first end 412 so as to achieve a desired degree of spreading of the second end 114 of the anchor body 110. In some embodiments, the second stop 128 can be located so that the second end 112 of the anchor body 110 achieves an expanded radius of approximately 40 millimeters, 20 millimeters, 10 millimeters, 7.2 millimeters, 5 millimeters, 2 millimeters, 1 millimeter, or any other desired diameter.

An axial bore 116 can include a third stop 128. As depicted in FIG. 3, a third stop 130 can be a wall perpendicular to the longitudinal axis 122 of the anchor body 110. As depicted in FIG. 3, the third stop 130 can be configured to provide an engageable surface to interact with portions of the expander (not shown) and thereby prevent the advancement of the expander (not shown) past a designated point. Advantageously, prevention of advancement of the expander (not shown) past a designated point allows consistent expansion of the anchor body 110 and prevents failure of the anchor 100 placement due to over penetration of the expander (not shown) into the anchor body 110.

Figure 4:
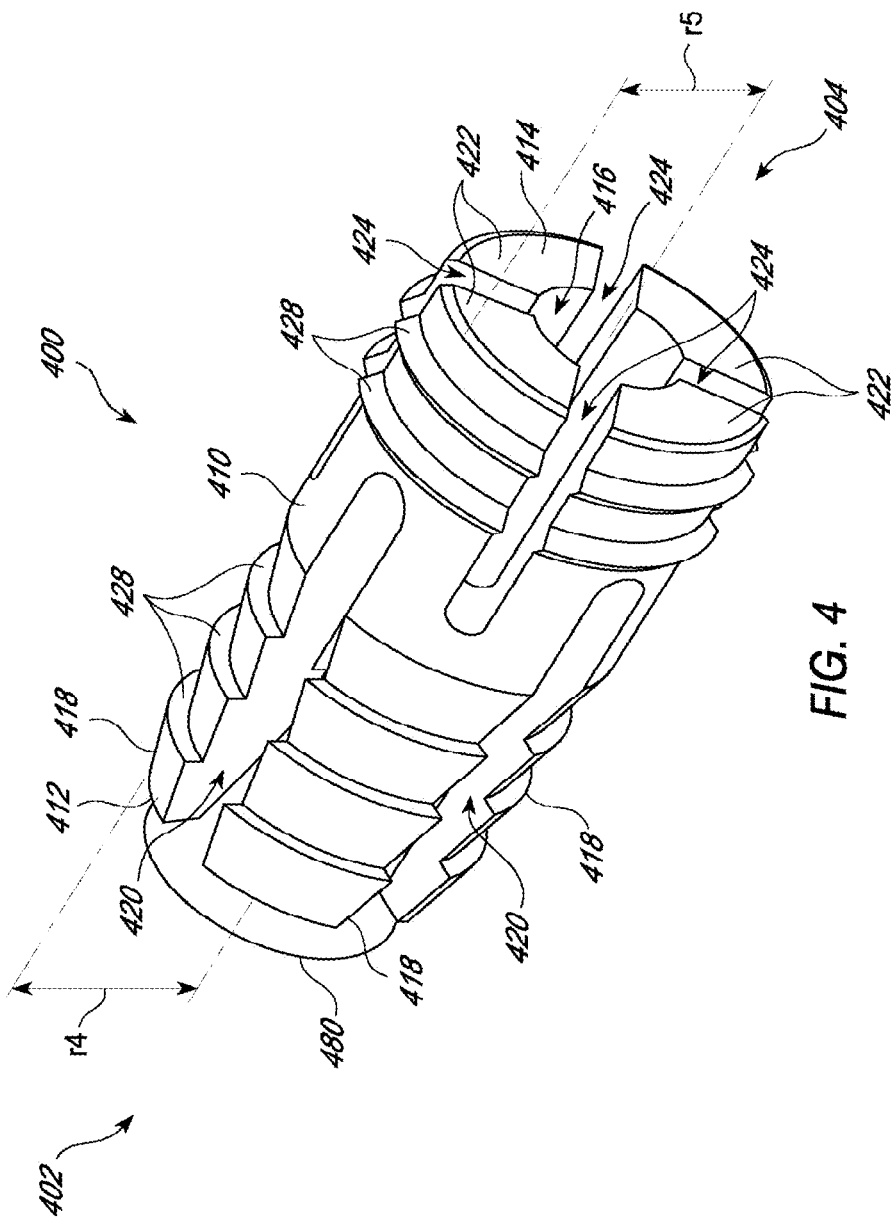
FIG. 4 depicts a perspective view of one embodiment of a tined dual expansion anchor in an undeployed or unexpanded state.

FIG. 4 depicts a perspective view of one embodiment of an unexpanded dual expansion anchor 400 comprising an anchor body 410 and an expander 480. The anchor has a distal end 402 and a proximal end 404.

The anchor body 410 has a first end 412 and a second end 414. In some embodiments, the first end 412 of the anchor body 410 is configured for placement into a hole in a bone. In some embodiments, the anchor 400 is placed in the hole in the bone so that the second end 414 is in closer proximity to the entrance hole into the bone than the first end 412. The anchor 400 depicted in FIG. 4 has a radius at the first end 412 of r4 and a radius at the second end 414 of r5. In some embodiments r4 and r5 are the same. In some embodiments, r4 and r5 are different.

Anchor 400 can be inserted into an anchor point with an insertion tool. In some embodiments, the second end 414 of the anchor body 410 is configured for interaction with a portion of the insertion tool to thereby allow placement of the anchor 400 at the anchor point. In some embodiments, the second end 414 of the anchor body 410 can be configured to abut portions of the insertion tool. The abutting interaction between the anchor body 410 and the insertion tool can facilitate a transfer of forces between the insertion tool and the anchor body 414, which transfer of forces can facilitate anchor insertion and/or result in deployment or expansion of the anchor 400.

The anchor body 410 depicted in FIG. 4 has an axial bore 416. The axial bore 416 can extend partially or entirely through the anchor body 410. In some embodiments, the axial bore 416 can be a first axial bore partially extending along the length of the anchor body 410 and a second axial bore partially extending along the length of the anchor body 410. The axial bore 416 depicted in FIG. 4 extends the entire length of the anchor body 410.

The axial bore 416 can be sized and dimensioned to receive the expander 480. The expander 480 depicted in FIG. 4 is partially disposed within the axial bore 416 of the anchor body 410.

The anchor body 410 depicted in FIG. 4 has plurality of first tines 418 extending from a position proximal to the second end 414 of the anchor body 410 to the first end 412 of the anchor body 410. Each of the first tines 418 is internally defined by the axial bore 416 and radially defined by a plurality of first expansion slots 420. An anchor body can include any desired number of first tines 418 and first expansion slots 420, including 10 or less, 5 or less, 4 or less, or two first tines 418 and first expansion slots 420. The anchor body 410 depicted in FIG. 4 has four first tines 418 and four first expansion slots 420.

The first tines 418 and first expansion slots 420 can be positioned at any desired radial position around the anchor body 410. In some embodiments, the first tines 418 and first expansion slots 420 can be positioned at regular intervals around the anchor body 410. In some embodiments, the first tines 418 and first expansion slots 420 can be irregularly positioned around the anchor body 410. FIG. 4 depicts an embodiment of an anchor body 410 in which the first tines 418 and first expansion slots 420 are equiangularly positioned around the anchor body 410.

Different embodiments of an anchor body 410 can additionally include first tines 418 and first expansion slots 420 of different lengths. In some embodiments, the first tines 418 and first expansion slots 420 of an anchor body 410 can have equal lengths. In some embodiments the first tines 418 and first expansion slots 420 may have different lengths. In some embodiments, the first tines 418 and first expansion slots 420 can be configured to have different lengths in that some of the first tines 418 may extend further from the second end 414 of the anchor body 410 toward the first end 412 of the anchor body 410 than other of the first tines 418. In some embodiments, the first tines 418 and first expansion slots 420 can have different lengths in that some of the first expansion slots 420 can extend further from the first end 412 of the anchor body 410 toward the second end 414 of the anchor body 410 than others of the first expansion slots 420. FIG. 4 depicts and embodiment of an anchor body 410 in which the first tines 418 and first expansion slots 420 have equal lengths.

The anchor body 410 depicted in FIG. 4 has plurality of second tines 422 extending from a position proximal to the first end 412 of the anchor body 410 toward the second end 414 of the anchor body 410. Each of the second tines 422 is internally defined by the axial bore 416 and radially defined by a plurality of second expansion slots 424. An anchor body can include any desired number of second tines 422 and second expansion slots 424, including 10 or less, 5 or less, 4 or less, or two second tines 422 and second expansion slots 424. The anchor body 410 depicted in FIG. 4 has four second tines 422 and four second expansion slots 424.

The second tines 422 and second expansion slots 424 can be positioned at any desired radial position around the anchor body 410. In some embodiments, the second tines 422 and second expansion slots 424 can be positioned at regular intervals around the anchor body 410. In some embodiments, the second tines 422 and second expansion slots 424 can be irregularly positioned around the anchor body 410. FIG. 4 depicts an embodiment of an anchor body 410 in which the second tines 422 and second expansion slots 424 are equiangularly positioned around the anchor body 410.

Different embodiments of an anchor body 410 can additionally include second tines 422 and second expansion slots 424 of different lengths. In some embodiments, the second tines 422 and second expansion slots 424 of an anchor body 410 can have equal lengths. In some embodiments the second tines 422 and second expansion slots 424 may have different lengths. In some embodiments, the second tines 422 and second expansion slots 424 can be configured to have different lengths in that some of the second tines 422 may extend further from the first end 414 of the anchor body 410 toward the second end 414 of the anchor body 410 than other of the second tines 422. In some embodiments, the second tines 422 and second expansion slots 424 can have different lengths in that some of the second expansion slots 424 can extend further from the second end 414 of the anchor body 410 toward the first end 412 of the anchor body 410 than others of the second expansion slots 424. FIG. 4 depicts and embodiment of an anchor body 410 in which the second tines 422 and second expansion slots 424 have equal lengths.

Some embodiments of an anchor body 410 can have a first set of tines 418 and a second set of tines 422 of equal length. Some embodiments of an anchor body 410 can have a first set of tines 418 and a second set of tines 422 of different lengths. FIG. 4 depicts one embodiment of an anchor body 410 in which the first set of tines 418 is longer than the second set of tines 422.

Some embodiments of an anchor body 410 can have first expansion slots 420 and second expansion slots 424 of equal length. Some embodiments of an anchor body 410 can have first expansion slots 420 and second expansion slots 424 of different lengths. FIG. 4 depicts one embodiment of an anchor body 410 in which the first expansion slots 420 are longer than the second expansion slots 424.

The first tines 418 and first expansion slots 420 and the second tines 422 and second expansion slots 424 allow the expansion of the anchor body 410 when the expander 480 is moved longitudinally in a direction from the first end 412 towards the second end 414 of the anchor body. When the anchor 400 is placed within a hole in a bone, the longitudinal displacement of the expander 480 towards the second end 414 of the anchor body 410 results in the radial expansion of the anchor body 410, and specifically results in the radial expansion of the first tines 418 and first expansion slots 420 located at the first end 412 of the anchor body and of the second tines 422 and second expansion slots 424 located at the second end 414 of the anchor body 410. In some embodiments, the anchor body 410 can be sized and dimensioned relative to the hole in which the anchor 100 is placed, so that the radial expansion of the anchor body resulting from the longitudinal displacement of the expander 480 towards the second end 414 causes the first tines 418 and the second tines 422 to engage with bone surrounding the hole in which the anchor 400 is positioned. In some embodiments, the engagement of the bone by the first tines 418 and the second tines 422 can be facilitated by teeth 428 located on some or all of the first tines 418 and/or the second tines 422. FIG. 4 depicts one embodiment of an anchor body 410 in which teeth 428 are located on all of the first tines 418 and the second tines 422. In some embodiments, the teeth (or ridges) 428 are designed to prevent the anchor 400 from displacing out of the bone. In some embodiments, the teeth 428 are designed to stabilize the anchor 400 in the bone. In some embodiments, the teeth 428 are designed to hold the anchored tissue in proximity to the bone. In some embodiments, the teeth 428 are designed to perform a combination of these and other functions.

In some embodiments, the teeth 428 may penetrate the bone, the teeth 428 may partially penetrate the bone, the teeth 428 may form depressions in the bone, or the teeth 428 may deform to fit to the bone.

In some embodiments, all of the teeth 428 on the anchor body 410 are similarly sized and dimensioned. An anchor body 410 may also have two or more types of teeth 428. Specifically, an anchor body 410 may have a first set of teeth located proximate to the first end 412 of the anchor body 410 on some or all of the first tines 418, and a second set of teeth located proximate to the second end 414 of the anchor body 410 on some or all of the second tines 422.

Figure 5:
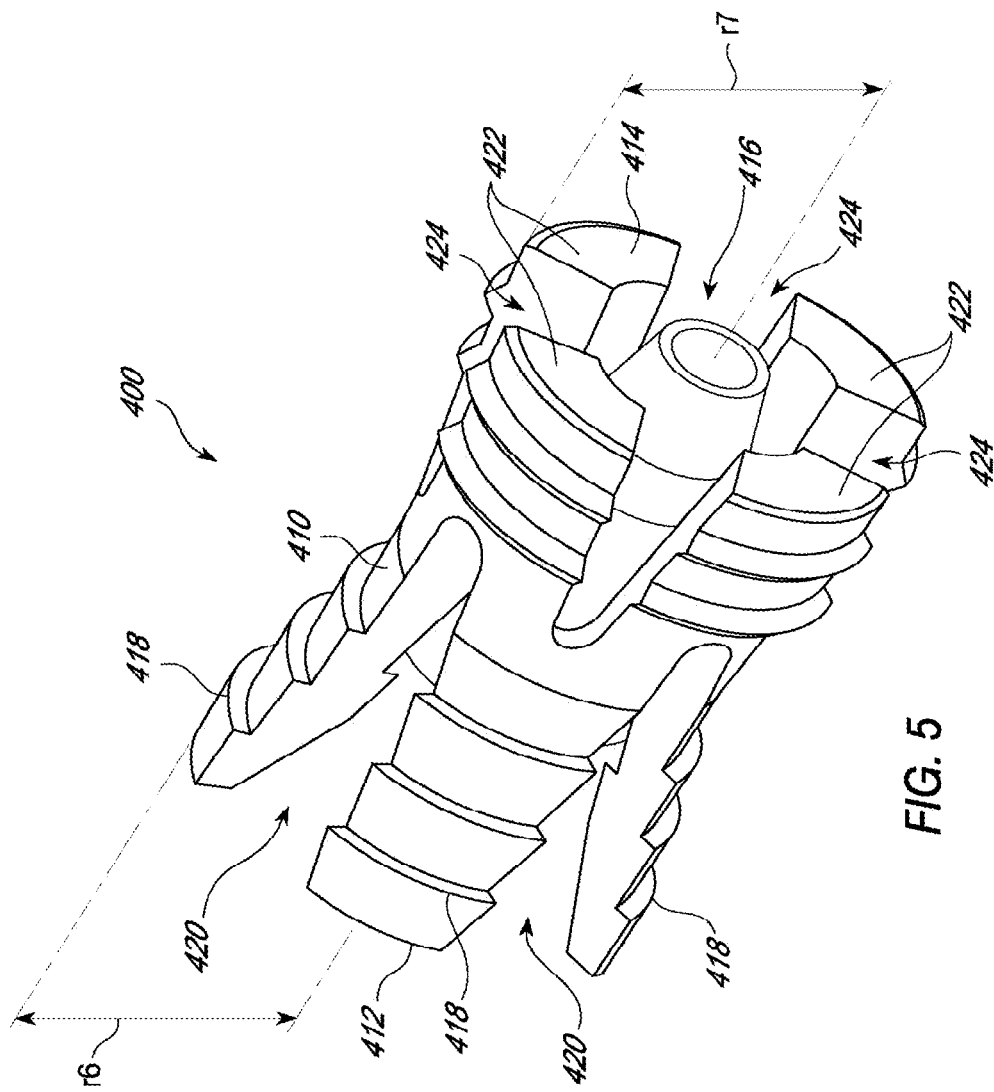
FIG. 5 depicts a perspective view of one embodiment of a tined dual expansion anchor in a deployed or expanded state.

FIG. 5 depicts a perspective view of one embodiment of the dual expansion anchor 400 comprising an anchor body 410 and an expander 480. The body 410 of the anchor 400 depicted in FIG. 5 has a first end 412, a second end 414, an axial bore 416, first tines 418, first expansion slots 420, second tines 422, second expansion slots 424, and teeth 428. As depicted in FIG. 5, the expander 480 is completely positioned within the axial bore 416 of the anchor body 410. With the expander 480 positioned completely within the axial bore 416 of the anchor body 410, the first end 412 of the anchor body 410 has a new radius r6 and the second end 414 of the anchor body 410 has a new radius r7. The expansion of the anchor body 410 caused by the new positioning of the expander 480 results in radius r6 at the first end 412 of the anchor body 410 being larger than radius r4 at the first end 412 of the anchor body 410 as depicted in FIG. 4, and in radius r7 at the second end 414 of the anchor body 410 being larger than radius r5 at the second end 414 of the anchor body 410 as depicted in FIG. 4. In some embodiments r6 and r7 are the same. In some embodiments r6 and r7 are different. Additionally, while FIGS. 4 and 5 depict an anchor 400 defined respectively by two radii r4, r5 or r6, r7, a person of skill in the art will recognize that a plurality of constant or non-constant radii can define some embodiments of an anchor 100. Thus, an expanded anchor 100 may have uniform or non-uniform radial expansion between a first end 112 and a second end 114.

Figure 6:
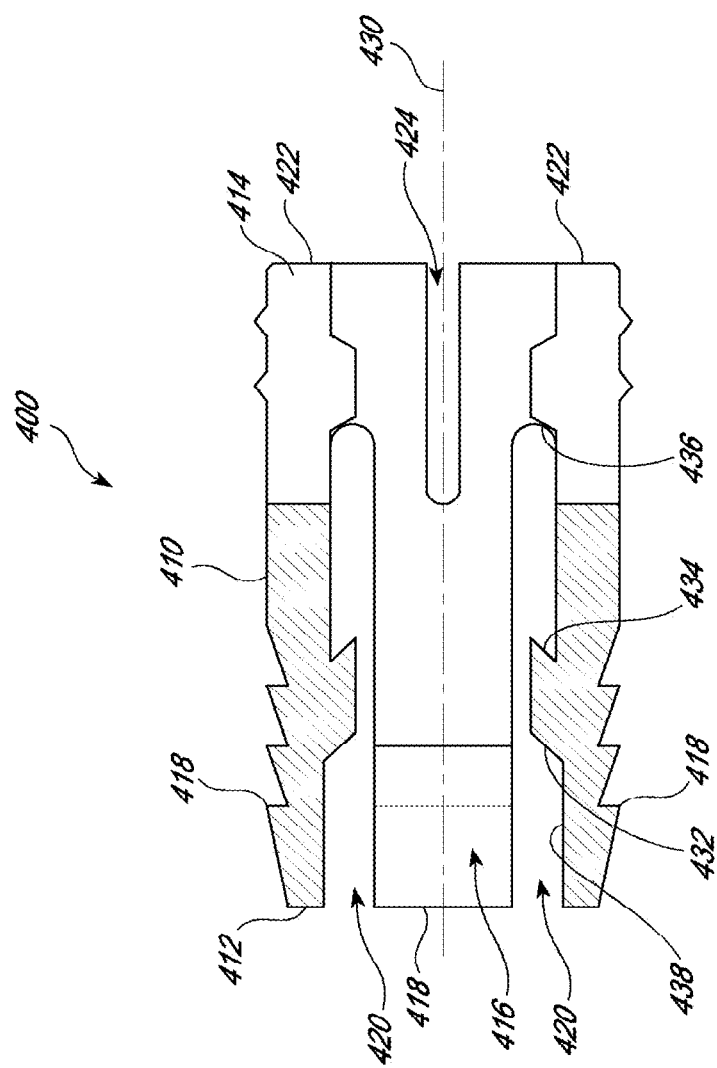
FIG. 6 depicts a cut-away view of one embodiment of a tined dual expansion anchor in an undeployed or unexpanded state.

FIG. 6 depicts a perspective cut-away view of the same embodiment of the dual expansion anchor 400 comprising an anchor body 410 configured for use with an expander (not shown). The body 410 of the anchor 400 depicted in FIG. 6 has a first end 412, a second end 414, an axial bore 416, first tines 418 and first expansion slots 420, second tines 422 and second expansion slots 424. An axial bore 416 has a longitudinal axis 430 and can comprise a variety of shapes and sizes. In some embodiments, an axial bore may have a single shape and constant diameter throughout the length of the anchor body 410. In some embodiments, and as depicted in FIG. 6, the shape and size of the axial bore 416 may vary along the length of the anchor body 410. A person of skill in the art will recognize that variations in the shape and size of the axial bore 416 can be used in connection with variations in the size and shape of the expander (not shown) to achieve desired expansion of the anchor body 410, to achieve desired placement of the expander (not shown) within the anchor body 410, and to facilitate and/or prevent certain movements of the expander (not shown) within the anchor body 410.

As depicted in FIG. 6, and axial bore 416 can comprise portions that are parallel to the longitudinal axis 430 of the axial bore 416, perpendicular to the longitudinal axis 430 of the axial bore 416, or angled relative to the longitudinal axis 430 of the axial bore 416. The axial bore 416 can comprise a first sloped portion 432. The first sloped portion 432 can be located proximate to the first end 412 of the anchor body 410, or as depicted in FIG. 6, separated from the first end 412 of the anchor body 410 by a parallel portion 438, parallel to the longitudinal axis 430 of the axial bore 416. The first sloped portion 432 can be configured to provide a cam surface for the expander (not shown) to facilitate movement of the expander (not shown) into the axial bore 416 and to thereby facilitate expansion of the radius of the first end 412 of the anchor body 410 from radius r4 to radius r6.

The axial bore 416 can include a first stop 434. As depicted in FIG. 6, a first stop 434 is a wall non-parallel to the longitudinal axis 430 of the anchor body 410. As depicted in FIG. 6, the first stop 434 can be configured to provide an engageable surface to interact with portions of the expander (not shown) and thereby prevent the expander (not shown) from retracting once the expander (not shown) has advanced past a designated point. Advantageously, prevention of the retraction of the expander (not shown) enables the permanent placement of an anchor 400 in bone.

A first stop can be located a desired distance from the first end 412 so as to achieve a desired degree of spreading of the first end 412 of the anchor body 410. In some embodiments, the first stop 434 can be located so that the first end 412 of the anchor body 410 achieves an expanded radius of approximately 40 millimeters, 20 millimeters, 10 millimeters, 5 millimeters, 2 millimeters, 1 millimeter, or any other desired diameter.

The axial bore 416 can comprise a second sloped portion 436. As depicted in FIG. 6, the second sloped portion 436 can be located proximate to the second end 414 of the anchor body 410. The second sloped portion 436 can be configured to provide a cam surface for the expander (not shown) to facilitate movement of the expander (not shown) down the axial bore 416 and to thereby facilitate expansion of the radius of the second end 414 of the anchor body 410 from radius r5 to radius r7. In some embodiments, the second end 414 of the anchor body 410 achieves an expanded radius of approximately 40 millimeters, 20 millimeters, 10 millimeters, 7.2 millimeters, 5 millimeters, 2 millimeters, 1 millimeter, or any other desired diameter.

Figure 7:
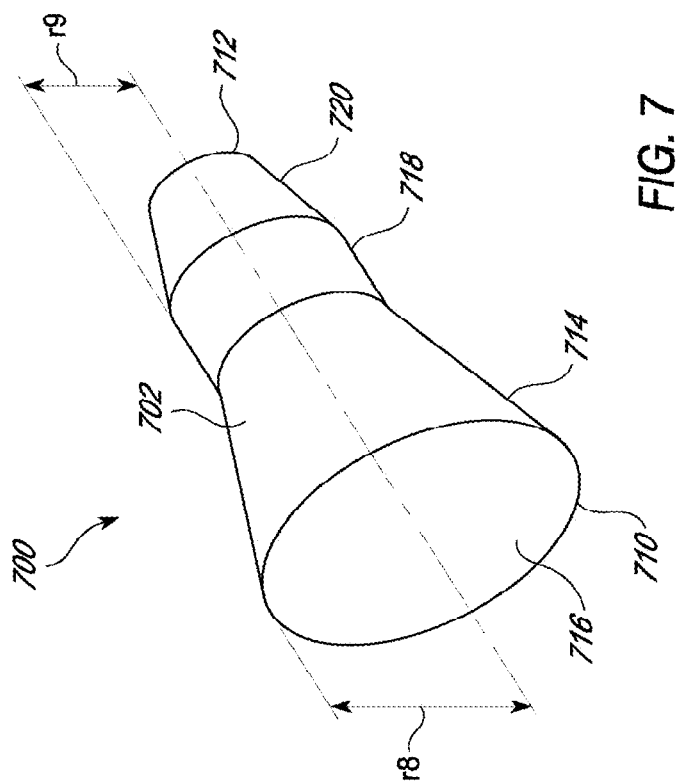
FIG. 7 depicts a perspective view of one embodiment of an expander.

An anchor can be used with a variety of expanders. FIG. 7 depicts one embodiment of an expander 700 comprising an expansion member 702 having a first end 710 and a second end 712. An expansion member 702 can have one or more features configured to cause expansion of an anchor body when the expander 700 is longitudinally displaced into the anchor body. The expander 700 depicted in FIG. 7 has a spreading head 714 having a radius r8 and located proximate to the first end 710 of the expansion member 702. The spreading head 714 can be manufactured to any desired size and shape. As depicted in FIG. 7, spreading head 714 can comprise a conical frustum having a base 716 located at the first end 710 of the expander. A person of skill in the art will recognize that the shape and size of the head 714 will affect the ultimate degree and shape of expansion of the anchor body, as well as the requisite forces to longitudinally displace the expander 700 within the anchor body.

In some embodiments, an expansion member 702 can include a shaft 718 having a diameter r9. As depicted in FIG. 7, shaft 718 can extend longitudinally from the spreading head 714 to the second end 712 of the expansion member 702. Shaft 718 can have a variety of sizes and shapes. The shaft 718 depicted in FIG. 7 is a conical shaft. In some embodiments, the shaft 718 can have a diameter r9 configured to fit within the axial bore of an anchor body without causing expansion of the anchor body. Thus, in some embodiments, expander 700 can be non-expandingly disposed within the axial bore of the anchor body when the shaft 718 is located in the axial bore and features of the expansion member 702 configured for expanding the anchor body are positioned so as to not cause expansion of the anchor body.

In some embodiments, and as depicted in FIG. 7, the shaft 718 can comprise a camming surface 720. In some embodiments, camming surface 720 can, for example, facilitate placement of the expander 700 in an axial bore of an anchor, or facilitate the expansion of the anchor body.

In some embodiments, an expander 700 can include features to facilitate application of forces to the expander 700 to affect deployment of the anchor. In some embodiments, an expander 700 can comprise a threaded hole in the second end 712 configured for threading engagement with a threaded portion of the insertion tool. In some embodiments of an anchor in which the anchor is deployed or expanded by the proximal movement of the expander 700 relative to the anchor, the anchor body can abut with a portion of the insertion tool so as to prevent movement of the anchor body relative to the insertion tool. The expander 700 can be connected to a portion of the insertion tool that is relatively moveable as compared to the portion of the insertion tool against which the anchor body abuts. In some embodiments, the abutting interaction of the anchor body and the insertion tool, and the connection of the expander 700 to a relatively moveable portion of the insertion tool can allow the longitudinal displacement of the expander from a first, undeployed, unexpended position proximate to the distal end of the anchor toward the proximate end of the anchor and to a second, deployed, expanded position.

Figure 7A:
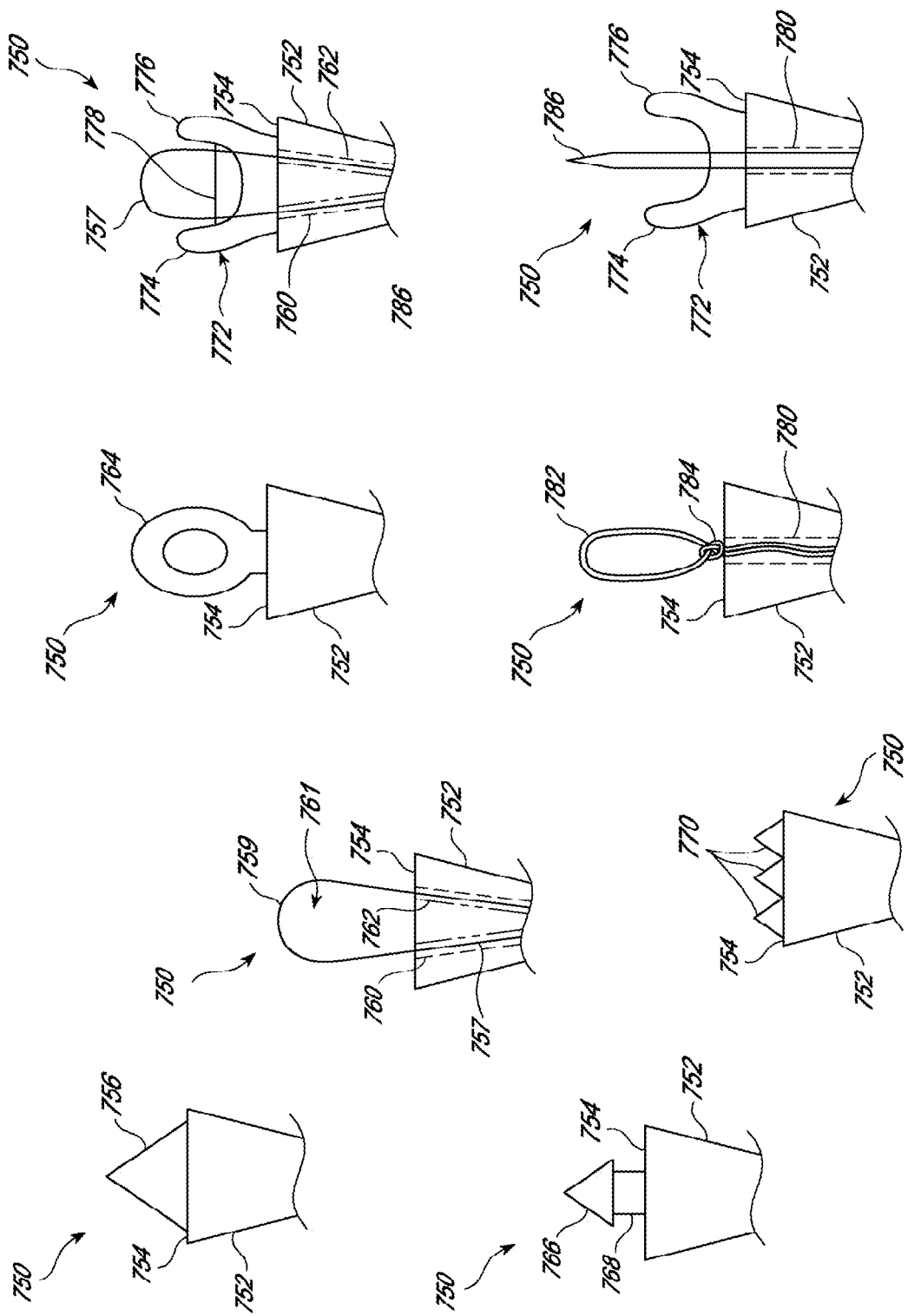
FIG. 7A depicts side views of several embodiments of a distal end of an expander.

An expander can include features configured for engaging with and capturing material to be secured to the bone, such as, for example, tissue or a suture. These features can be located on a variety of portions of the expansion member 702, including, for example, the head 714, shaft 718, or any other feature configured for expansion. FIG. 7A depicts several embodiments of features configured for engaging with material to be secured to the bone, such as, for example, tissue or a suture, mounted on the base of the head of the expansion member. In some embodiments, an expander 750 can comprise a head 752 having a base 754. In some embodiments, the expander 750 can further include a penetrating member 756 extending from the base 754 of the spreading head 752. The penetrating member 756 can comprise a variety of sizes and shapes. As depicted in FIG. 7A, the penetrating member 756 comprises a feature having a triangular cross-section, such as, for example, a feature comprising a cone, a triangular pyramid, a square pyramid, or a rectangular pyramid. The penetrating member 756 can be configured for deforming the material to be secured to the bone, or for piercing a hole into or through the material to be secured to the bone.

In some embodiments, the expander 750 can include a first hole 760 and a second hole 762. Holes 760, 762 can comprise a range of sizes and shapes, and can be configured for allowing threading of the material to be secured to the bone or a securement feature, such as, for example, a suture, through the holes 766, 768. As also depicted in FIG. 7A, in some embodiments of the expander 750, a suture 757 can pass through the first hole 760 and the second hole 762 to form a loop 759, which, in combination with base 754 defines an encircled area 761 through which a tendon or other material to be secured to the bone can be passed. A tendon, or other material to be secured to the bone can be passed through the encircled area 761 and the ends of the suture 757 can be tensioned to constrict the loop 759 and thereby secure the material to be secured to the bone in the loop 759 and against the base 754. The suture 757 can then be secured to prevent loosening of the suture 757 and release of the tendon or other material to be secured to the bone.

In some embodiments, the expander 750 can further include a loop member 764 extending from the base 754 of the spreading head 722. The loop member 764 can comprise a variety of sizes and shapes. As depicted in FIG. 7A, the loop member 764 can comprise an elongated torus. The loop member 764 as depicted in FIG. 7A can be configured for allowing threading of the material to be secured to the bone or a securement feature, such as, for example, a suture, through the loop member 764.

In some embodiments, the expander 750 can further include a retention penetrating member comprising a penetrating element 766 and a shaft element 768 extending from the base 754 of the spreading head 752. The retention penetrating member can comprise a variety of sizes and shapes. As depicted in FIG. 7A, the retention penetrating member comprises a penetrating element 766 having a triangular cross-section, such as, for example, a feature comprising a cone, a triangular pyramid, a square pyramid, or a rectangular pyramid. As depicted in FIG. 7A, the larger size the penetrating element 766 as compared to the shaft element 768 can create a retention penetrating member capable of facilitating penetration of the material to be secured to the bone and hindering the retraction of the retention penetrating member from the material to be secured to the bone after penetration.

In some embodiments, the expander 750 can further include a plurality of penetrating members 770 extending from the base 754 of the spreading head 752. The penetrating members 770 can comprise a variety of sizes and shapes. As depicted in FIG. 7A, the penetrating members 770 comprises features having a triangular cross-section, such as, for example, a feature comprising a cone, a triangular pyramid, a square pyramid, or a rectangular pyramid. In some embodiments, the penetrating members 770 can be each configured to create punctuate contact, linear contact, or any other type of desired contact with the material to be secured. In embodiments in which the penetrating members 770 are configured for punctuate contact, each of the penetrating members 770 can be configured to extend to a point. In embodiments in which the penetrating members 770 are configured for linear contact, each of the penetrating members may linearly stretch across base 754 of the spreading head 752 and extend to a linear edge. The penetrating members 770 can be configured for deforming the material to be secured to the bone, or for piercing a hole into or through the material to be secured to the bone.

In some embodiments, the expander 750 can comprise a first hole 760 and a second hole 762, both extending through the spreading head 752 of the expander 750, a suture 757 passing through the first hole 760 and the second hole 762, and a stirrup 774 extending from the base 754 of the spreading head 752 of the expander 750. The stirrup 772 can comprise a first prong 774 and a second prong 776. In some embodiments, the stirrup 772 can be configured to facilitate the retention of material for securing to a bone between the first prong 774 and the second prong 776. The stirrup 772, and the first and second prongs 774, 776 can comprise a variety of shapes and sizes, and can be made from a variety of materials.

The stirrup 772 can be configured for different degrees of movement relative to the anchor. In some embodiments, the stirrup 772 can be configured to partially fit within the anchor when the anchor is deployed, and in some embodiments, the stirrup 772 may be wholly outside of the anchor when the anchor is deployed. In some embodiments, the stirrup 772 can be static and in some embodiments, the stirrup 772 can be dynamic. In some specific embodiments, the first and second prongs 774, 776 can be static and/or dynamic relative to each other.

In some embodiments, the stirrup 772 can further comprise a shelf 778. The shelf 778 can extend between the first and second prongs 774, 776. In some embodiments, the shelf 778 can be configured to facilitate in bending of the material to be secured to the bone, and can advantageously prevent the material from moving relative to the shelf 778 while securing the material to the bone.

The shelf 778 can comprise a variety of shapes and sizes. In some embodiments, the shelf 778 can have a rectangular cross-section, a triangular cross-section, a trapezoidal cross-section, or have any other desired cross-sectional shape.

In some embodiments, the expander 750 can comprise a first hole 780 extending through the spreading head 752 of the expander 750. The first hole 780 can comprise a variety of shapes and sizes, and can be located in a variety of positions on the spreading head 752. As depicted, the first hole 780 can extend axially through the spreader head 752.

In some embodiments, the expander 750 can further comprise a suture 757 extending through the first hole 780. In some embodiments, the suture 757 can be formed into a loop 782 and can be manipulated into a knot 784. In some embodiments, the knot 784 can be performed before a procedure using the expander 750, and in some embodiments, the knot 784 can be formed during the procedure. In some embodiments, the knot 784 can be configured to maintain a constant size of the loop 782, and in some embodiments, the knot 784 can be configured to allow the loop 782 to change size. In some embodiments, the loop 782 can be configured to receive and retain the material that is to be secured to the bone. Advantageously, in some embodiments, the size of the suture 757 and the size of the knot 784 can prevent the loop 782 of the suture 757 from moving through the first hole 780 of the expander 750.

In some embodiments, the expander 750 can comprise a stirrup 772 comprising a first prong 774 and a second prong 776, a first hole 780, and a spike 786. The spike 786 can be configured to retain material that is positioned between the first and second prongs 774, 776. In some embodiments, the spike 786 can be configured to retain the material positioned between the first and second prongs 774, 776 by piercing that material.

The spike 786 can comprise a variety of shapes and sizes and can be made from a variety of materials. In some embodiments, the spike can be sized and shaped to be positionable via the first hole 780 between the first prong 774 and the second prong 776.

In some embodiments, the expander can comprise a combination of the above disclosed features configured for engaging with and capturing material to be secured to the bone. Thus, in some embodiments, an expander may include, for example, one or several penetrating members and a suture or loop member. A person skilled in the art will recognize that the present disclosure contemplates a variety of different combination of features configured for engaging with and capturing material to be secured to the bone, and is not limited to the specific embodiments outlined above.

Figure 7B:
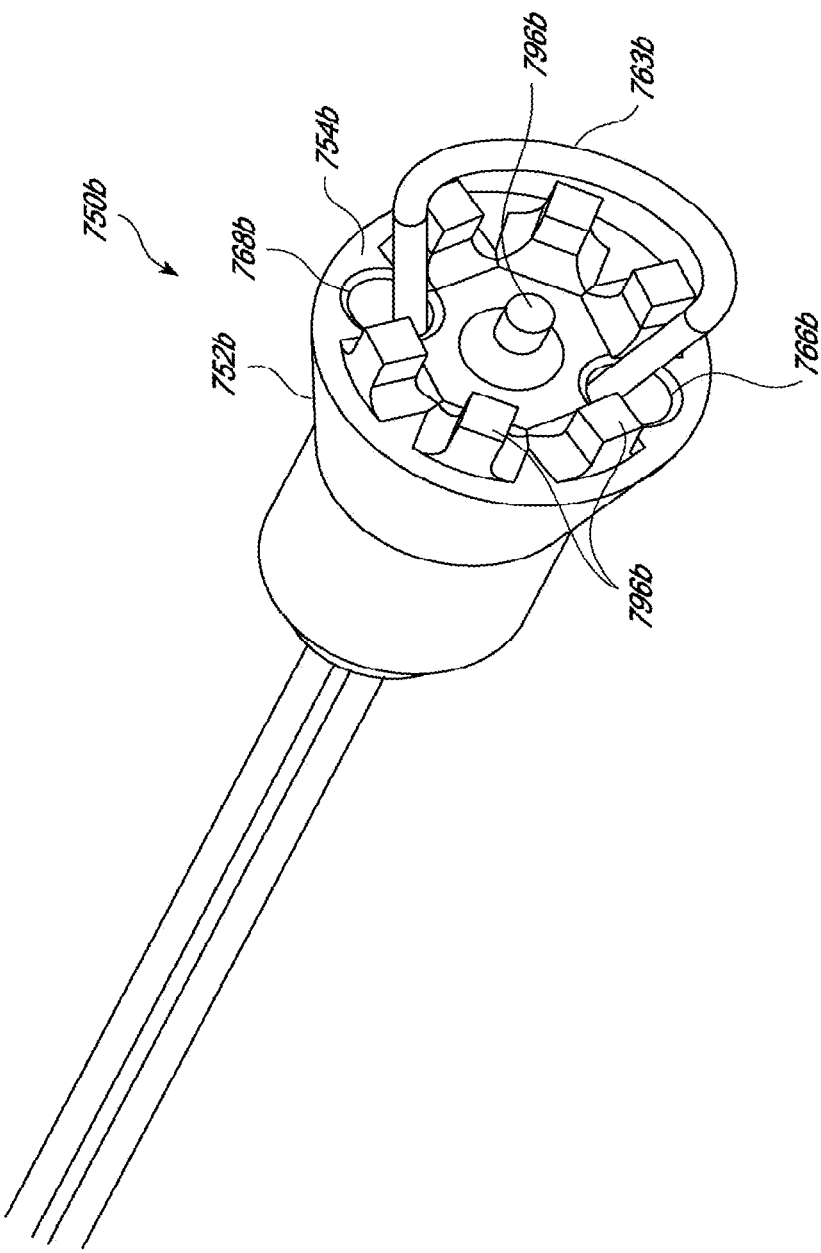
FIG. 7B depicts a perspective view of one embodiment of a distal end of an expander.

FIG. 7B depicts one such hybrid embodiment of an expander including multiple features configured for engaging with and capturing material to be secured to the bone. As depicted in FIG. 7B, expander 750b comprises a head 752b having a base 754b. The expander 750b further includes a plurality of penetrating members 796b extending from the base 754b of the spreading head 752b. As seen in FIG. 7B, these penetrating members 796b can comprise a variety of shapes and dimensions. As further seen in FIG. 7B, base 754b further comprises a first hole 766b and a second hole 768b configured to receive a suture to form suture loop 763b. A tendon, or other material to be secured to the bone can be passed through the suture loop 763b and over penetrating member 796b. Further, tension of the suture loop 763b increases the force with which the secured material contacts the penetrating members 796b, and thereby further secures the material.

Figure 8:
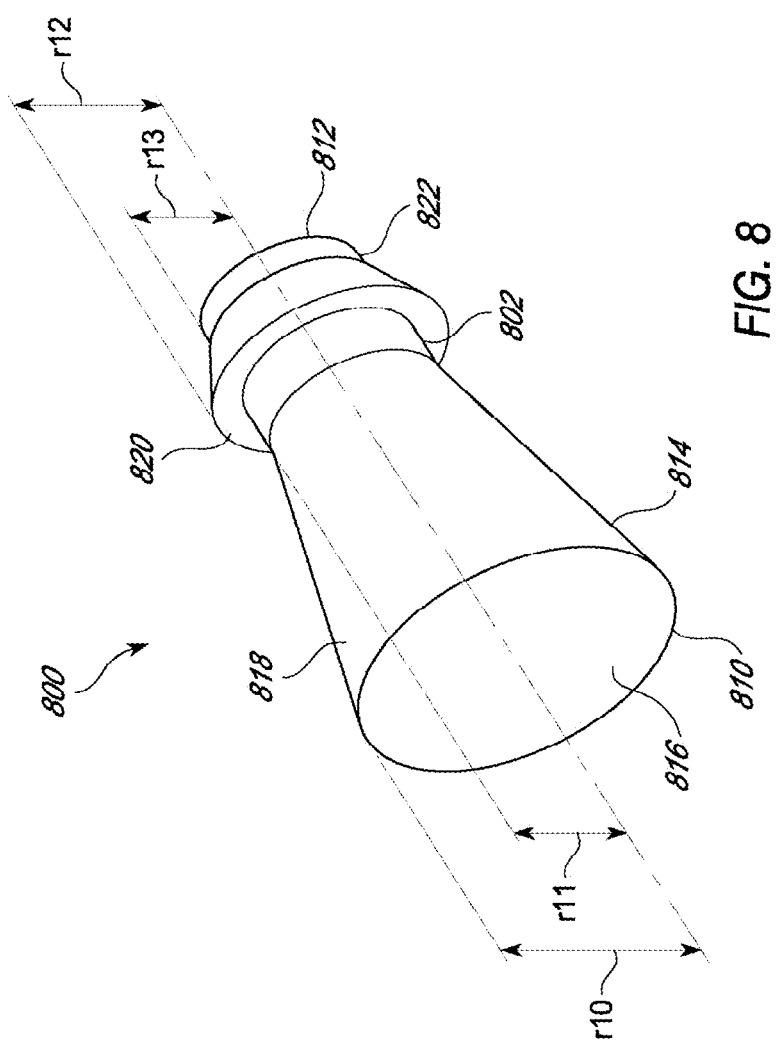
FIG. 8 depicts a perspective view of one embodiment of a single piece expander.

FIG. 8 depicts one embodiment of a single piece expander 800 comprising and expansion member 802 having a first end 810 and a second end 812. The expansion member 802 further comprises a spreading head 814 having a radius r10 and having a base 816, a first shaft portion 818 having a radius r11, an spreading shoulder 820 having a radius r12, and a second shaft portion 822 having a radius r13. The spreading head 814 depicted in FIG. 8 comprises a conical frustum having a base at the first end 810 of the single piece expander 800. The base 816 of the spreading head 814 depicted in FIG. 8, is radially elevated above the first shaft portion 818, above the spreading shoulder 820, and above the second shaft portion 822, in that the radius r10 of the base 816 of the spreading head 814 is larger than the radius r11 of the first shaft portion 818, larger than the radius r12 of the spreading shoulder 820, and larger than the radius r13 of the second shaft portion 822. The spreading head 814 can comprise a variety of sizes and shapes and a variety of relative sizes according to application requirements for an anchor.

The expansion member 802 depicted in FIG. 8 comprises a spreading shoulder located between the first end 810 and the second end 812 of the single piece expander 800. However, in other embodiments, the spreading shoulder 820 can be located in other positions on the single piece expander 800, including, at the second end 812 of the single piece expander 800. The spreading shoulder 820 depicted in FIG. 8 is radially elevated above the first shaft portion 818 and above the second shaft portion 822 in that the radius r12 of the spreading should 820 is larger than the radius r11 of the first shaft portion 818 and larger than the radius 813 of the second shaft portion 822. The spreading shoulder 822 can comprise a variety of sizes and shapes and a variety of relative sizes according to application requirements for an anchor. In some embodiments, the spreading shoulder 822 can be radially smaller than, radially equal to, or radially larger than the base 816 of the spreading head 814, than the first shaft portion 818, or than the second shaft portion 822 Likewise, the shapes and dimensions of the other features of the single piece expander can be varied to achieve desired results.

Figure 8A:
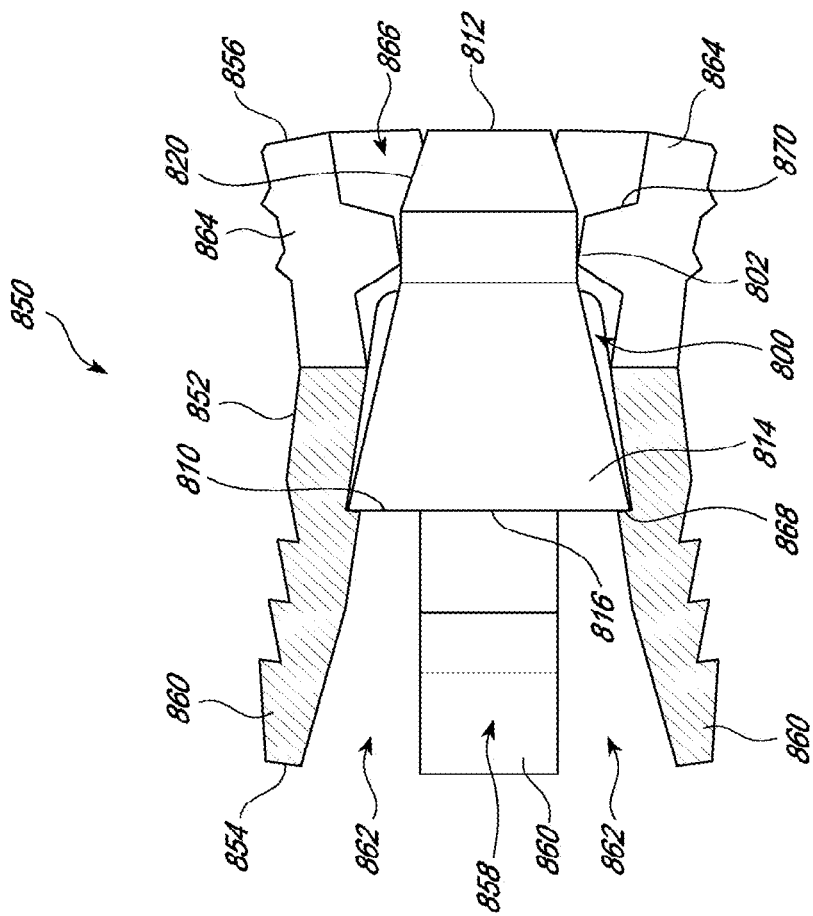
FIG. 8A depicts a cut-away view of one embodiment single piece expander deploying a tined dual expansion anchor.

FIG. 8A depicts a perspective cut-away view of an anchor 850 comprising an anchor body 852 and an expander 800 in an expanded or deployed configuration.

The expander depicted in FIG. 8A comprises an expansion member 802 having a first end 810 and a second end 812. The expansion member 802 further comprises a spreading head 814 having a base 816 located at the first end 810. The expansion member additionally comprises a camming surface 820 located proximate to the second end 812 of the expansion member 802 and between the first end 810 of the expansion member 802 and the second end 812 of the expansion member 802.

The anchor body 852 depicted in FIG. 8A comprises a first end 854, a second end 856, an axial bore 858, first tines 860 and first expansion slots 862, second tines 864 and second expansion slots (not shown). The axial bore 858 of the anchor body 852 depicted in FIG. 8A also has a first stop 868 and a camming abutment 870.

As depicted in FIG. 8A, the expander 800 is wholly positioned within the axial bore 858 of the anchor body 850. Specifically, the expander 800 is positioned within the axial bore 858 of the anchor body 850 such that the first stop 868 prevents movement of the expander 800 towards the first end 854 of the anchor body 850 by abuttingly engaging with the base 816 of the spreading head 814 of the expander 800.

As depicted in FIG. 8A, the spreading head 814 and other portions of the expander 800 expandingly engage with portions of the axial bore to deploy or expand the anchor body 850.

Figure 9:
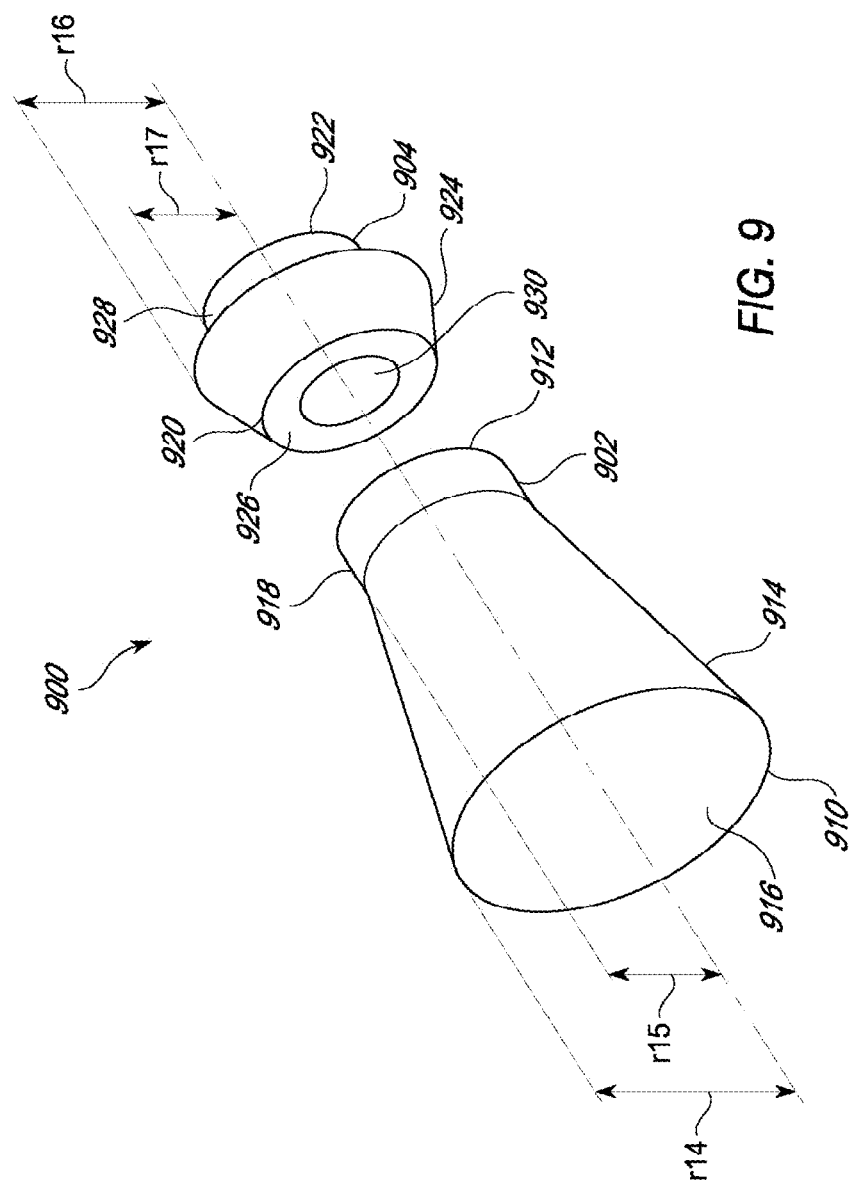
FIG. 9 depicts a perspective view of one embodiment of a two piece expander.

FIG. 9 depicts one embodiment of a two piece expander 900 comprising a first expansion member 902 and a second expansion member 904. In some embodiments, a two piece expander 900 can include features to facilitate application of forces to the expander 900 to affect deployment of the anchor. In some embodiments of an anchor in which the anchor is deployed, or expanded, by the movement of the expander 900 relative to the anchor, the anchor body can abut with a portion of the insertion tool so as to prevent movement of the anchor body relative to the insertion tool. The pieces of the expander 900 can be connected to one or multiple portions of the insertion tool that are relatively moveable as compared to the portion of the insertion tool against which the anchor body abuts. In some embodiments, the abutting interaction of the anchor body and the insertion tool, and the connection to the pieces of the expander 900 allow the relatively moveable portion of the insertion tool to longitudinally displace the expander pieces from a first, undeployed, unexpanded position to a second, deployed, expanded position.

The first expansion member has a first end 910 and a second end 912. The first expansion member 902 has a first spreading head 914 having a base 916 defined by a radius r14, and a first shaft portion 918 defined by a radius r15. The first spreading head 914 depicted in FIG. 9 comprises a conical frustum having a base 916 at the first end 910 of the first expansion member 902 of the double piece expander 900. The base 916 of the first spreading head 914 depicted in FIG. 9, is radially elevated above the first shaft portion 918 in that the radius r14 of the base 916 of the first spreading head 914 is larger than the radius r15 of the first shaft portion 918. The first spreading head 914 can comprise a variety of sizes and shapes and a variety of relative sizes according to application requirements for an anchor.

The second expansion member 904 has a first end 920 and a second end 922. The second expansion member 904 has a second spreading head 924 having a base 926 defined by a radius r16, and a second shaft portion 928 defined by a radius r17. The second spreading head 924 depicted in FIG. 9 comprises a conical frustum having a base 926 at the first end 920 of the second expansion member 904 of the double piece expander 900. The base 926 of the second spreading head 924 depicted in FIG. 9, is radially elevated above the second shaft portion 928 in that the radius r16 of the base 926 of the second spreading head 924 is larger than the radius r17 of the second shaft portion 928. The second spreading head 924 can comprise a variety of sizes and shapes and a variety of relative sizes according to application requirements for an anchor. The first and second spreading heads 914, 924 can comprise a variety of sizes and shapes and a variety of relative sizes according to application requirements for an anchor. In some embodiments, the base 916 of the first spreading head 914 can be radially smaller than, radially equal to, or radially larger than the base 926 of the second spreading head 924. Similarly, the relative sizes of the first shaft portion 918 and the second shaft portion 928 can vary with respect to each other and with respect to the first and second spreading heads 914, 924.

In some embodiments of a double piece expander 900, the second expansion member can comprise a thru-hole 930. The thru-hole can be sized and shaped to allow a portion of the insertion tool configured for attachment to the first expansion member 902 to pass through the second expansion member 904.

In some additional embodiments, the second end 922 of the second expansion member 904 can be configured for abutting contact with a portion of an insertion tool. In some embodiments, the portion of the insertion tool can be configured to allow movement of the second expansion member 904 relative to the anchor body.

Figure 9A:
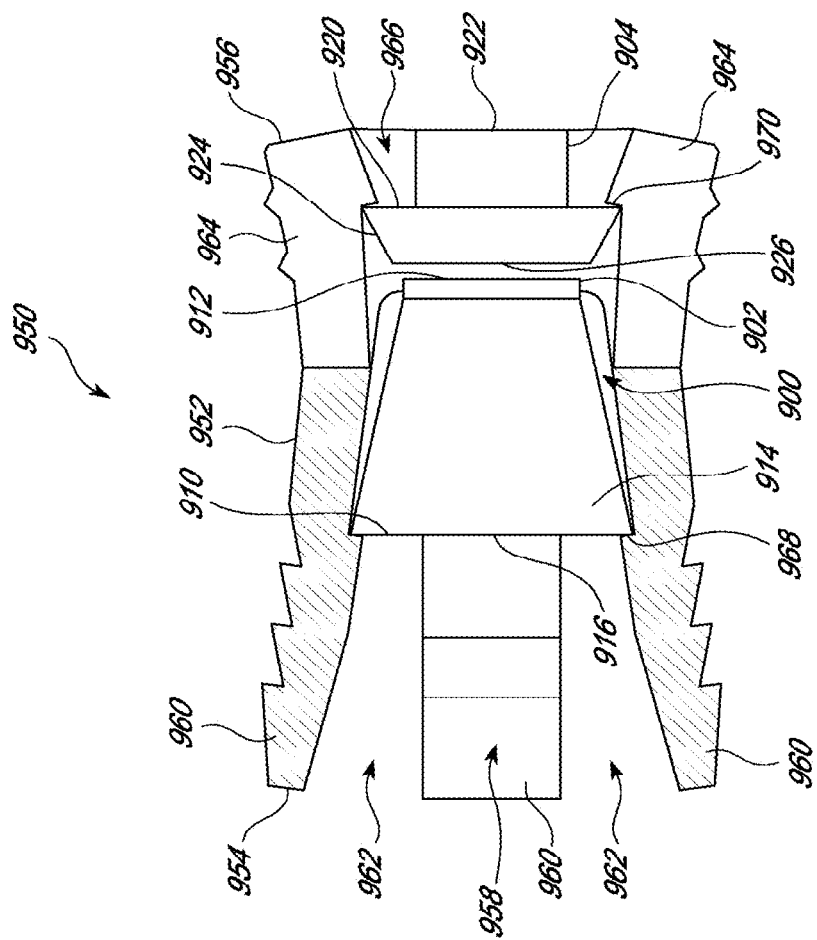
FIG. 9A depicts a cut-away view of one embodiment of a two piece expander deploying a tined dual expansion anchor.

FIG. 9A depicts a perspective cut-away view of an anchor 950 in an expanded or deployed configuration comprising an anchor body 952 and a double piece expander 900.

The double piece expander 900 depicted in FIG. 9A comprises a first expansion member 902 and a second expansion member 904. The first expansion member 902 has a first end 910 and a second end 912 and comprises a first spreading head 914 having a base 916 located at the first end 910. The second expansion member 904 has a first end 920 and a second end 922 and comprises a second spreading head 924 having a base 926 located at the first end 920.

The anchor body 952 depicted in FIG. 9A comprises a first end 954, a second end 956, an axial bore 958, first tines 960 and first expansion slots 962, second tines 964 and second expansion slots (not shown). The axial bore 958 of the anchor body 952 depicted in FIG. 9A also has a first stop 968 and a second stop 970.

As depicted in FIG. 9A, the expander 900 is wholly positioned within the axial bore 958 of the anchor body 950. Specifically, the expander 900 is positioned within the axial bore 958 of the anchor body 950 such that the first stop 968 prevents movement of first expansion member 902 towards the first end 954 of the anchor body 950 by abuttingly engaging with the base 916 of the first spreading head 914 of the first expansion member 902. The second expansion member 904 of the expander 900 is positioned within the axial bore 958 of the anchor body 950 such that the second stop 970 prevents movement of second expansion member 904 towards the second end 956 of the anchor body 950 by abuttingly engaging with the second spreading head 924 of the second expansion member 904. As additionally depicted in FIG. 9A, the first expansion member 902 is not in contact with second expansion member 904. However, a person of skill in the art will recognize that in some embodiments, a first expansion member 902 may be in contact with a second expansion member 904.

As depicted in FIG. 9A, the first spreading head 914 and the second spreading head 924 expandingly engage with portions of the axial bore to deploy or expand the first tines 960 and first expansion slots 962 located at the first end 954 of the anchor body 950 and the second tines 964 and second expansion slots 966 located at the second end 956 of the anchor body 950 respectively.

The above described dual expansion anchor can be made from a variety of materials, including, natural, or manmade materials. The dual expansion anchor can be made of metal, plastic, polymer, composite, or other materials. In some embodiments, the anchor is made of a biocompatible polymer, plastic, or metal. Other embodiments include a tissue capture anchor entirely or in part of a non-metallic substance that is biocompatible. Biocompatible materials such as poly ether ketone (PEK), polyether ether ketone (PEEK), polyetherimide (ULTEM), ultrahigh molecular weight polyethylene (UHMPE), polyphenylene, or some other engineering polymer materials known to those of skill in the art may be used. A non-metallic anchor system may provide certain advantages such as, for example, eliminating MRI artifacts.

Figure 10:
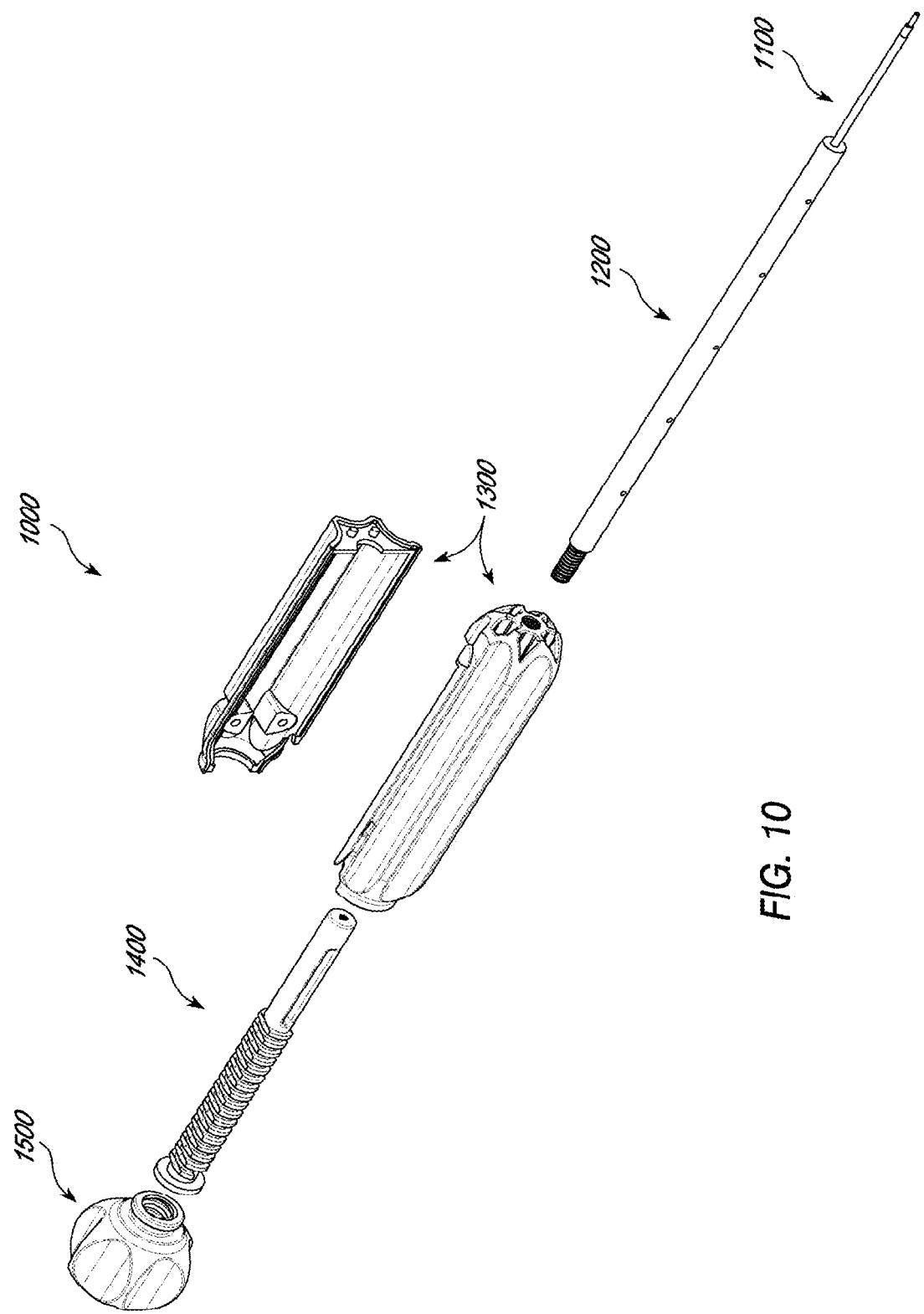
FIG. 10 depicts and exploded perspective view of one embodiment of an inserter tool.

FIG. 10 depicts individual components of one embodiment of an inserter tool. An inserter tool comprises a range of features configured to allow the inserter tool to insert an anchor and then deployingly interact with the anchor. One embodiment of an inserter tool may be configured for use with a specific anchor configuration, or with a specific spreader configuration. FIG. 10 depicts an embodiment of an inserter configured for use with a single piece expander. The inserter tool comprises an inner rod or tube 1100, an outer tube 1200, a handle body 1300, a threaded actuator shaft 1400, and a deployment knob 1500. In some embodiments, the inserter 1000 is coupled to the anchor during manufacturing. In a preferred embodiment, the inserter tool is disposable.

The inserter tool 1000 is designed to insert and manipulate an anchor such as the anchor described in FIGS. 1 through 6. In some embodiments, the anchor is manufactured to be attached to an inserter tool before packaging. In other embodiments, the tissue capture anchor is coupled to the inserter tool prior to insertion. In a basic configuration, the inserter tool is assembled as follows: the inserter tool 1000 is configured such that the inner rod 1100 is disposed within the outer tube 1200. The outer tube is configured to fit against the proximal end of the anchor. The inner rod 1100 extends through outer tube 1200 and is configured to attach to the expander via threading on both the proximal hole in the expander and threading on the distal end of the inner rod 1100. The proximal end of the outer tube 1200 is connected to a handle 1300 and the inner rod 1100 extends through the proximal end of the outer tube 1200 and screws into the threaded actuator shaft 1400. The actuator shaft 1400 extends just past the proximal end of the handle 1300 where it is configured to secure with a deployment knob 1500.

The individual components of the inserter tool are further described in detail below.

Figure 10A:
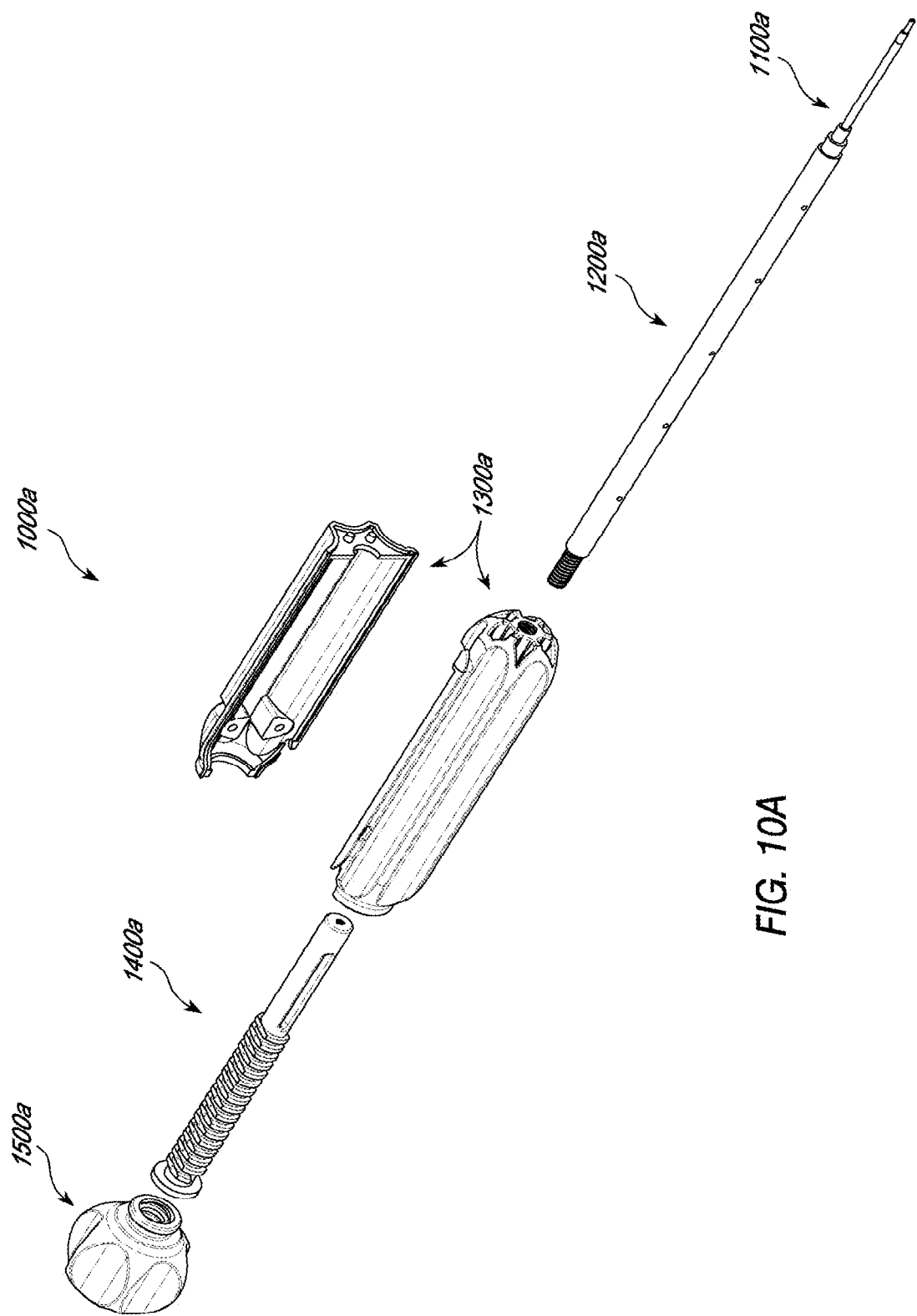
FIG. 10A depicts and exploded perspective view of one embodiment of an inserter tool configured for use with a two piece expander.

FIG. 10A depicts an embodiment of an inserter configured for use with a two piece expander. Like the inserter tool 1000 depicted in FIG. 10, inserter tool 1000a comprises an inner rod or tube 1100a, an outer tube 1200a, a handle body 1300a, a threaded actuator shaft 1400a, and a deployment knob 1500a. In some embodiments, the inner rod or tube 1100a, the outer tube 1200a, the handle body 1300a, the threaded actuator shaft 1400a, and the deployment knob 1500a of inserter tool 1000a can fit together as described in relation to those features of FIG. 10. In some embodiments, some or all of the inner rod or tube 1100a, the outer tube 1200a, the handle body 1300a, the threaded actuator shaft 1400a, and the deployment knob 1500a of inserter tool 1000a can include additional features configured to facilitate use with a two piece expander. These differences can include, for example, additional features located on the outer tube 1200a, or on any other feature of the inserter tool 100a. Additional features of the outer tube 1200a will be discussed in greater detail below.

Figure 11:
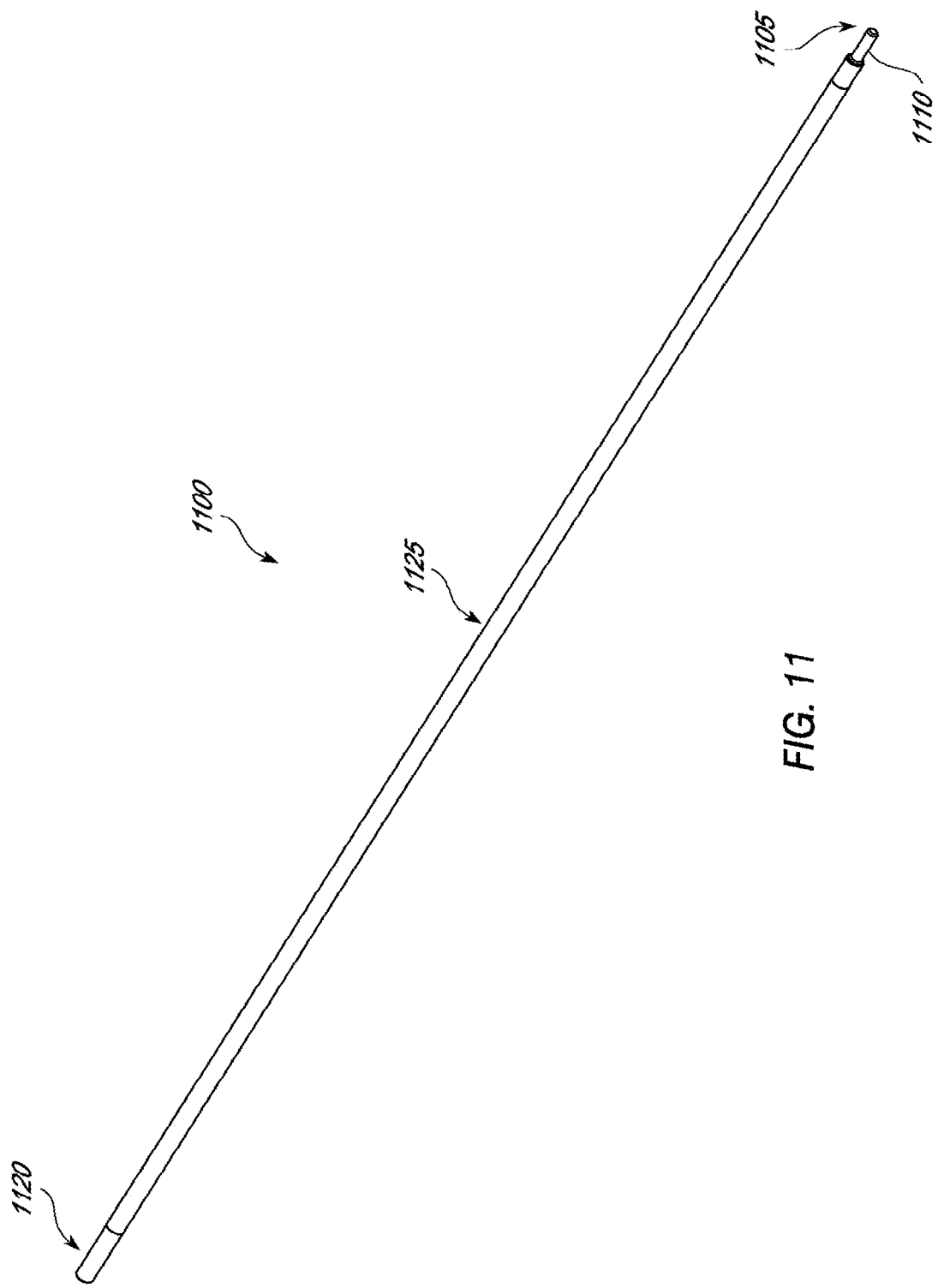
FIG. 11 is a perspective view of one embodiment of an inner rod.

FIG. 11 shows a perspective view of an embodiment of the inner rod 1100. In some embodiments, the inner rod is an inner tube. The inner rod comprises a distal end configured to secure to the expander, a proximal end which is configured to interact with the other components of the inserter, for instance the actuator shaft 1400. The inner rod 1100 is configured that a proximal end 1120 is advanced through the outer tube 1200 and into the handle 1300 where it is further secured within the actuator shaft 1400 via threading. The distal end 1105 of the inner rod 1100 is configured to be advanced through the central hole in the anchor body and then secured to the expander until the anchor is fully deployed and the inner rod 1100 is separated from the anchor. In some embodiments, the distal end 1106 can comprise features configured to engage with the expander, such as, for example, threads 1110. The body 1125 of the inner rod 1100 is configured for sliding positioning within outer tube 1200.

The inner rod 1100 extends through the central hole in the anchor body before coupling with the expander. In one embodiment, the inner rod 1100 couples with the expander through threads on the end of the inner rod 1100 and within the proximal end of the expander. In other embodiments, the inner rod 1100 may couple to the expander through other securing mechanisms such as adhesives, welding or frictional fit.

Figure 12:
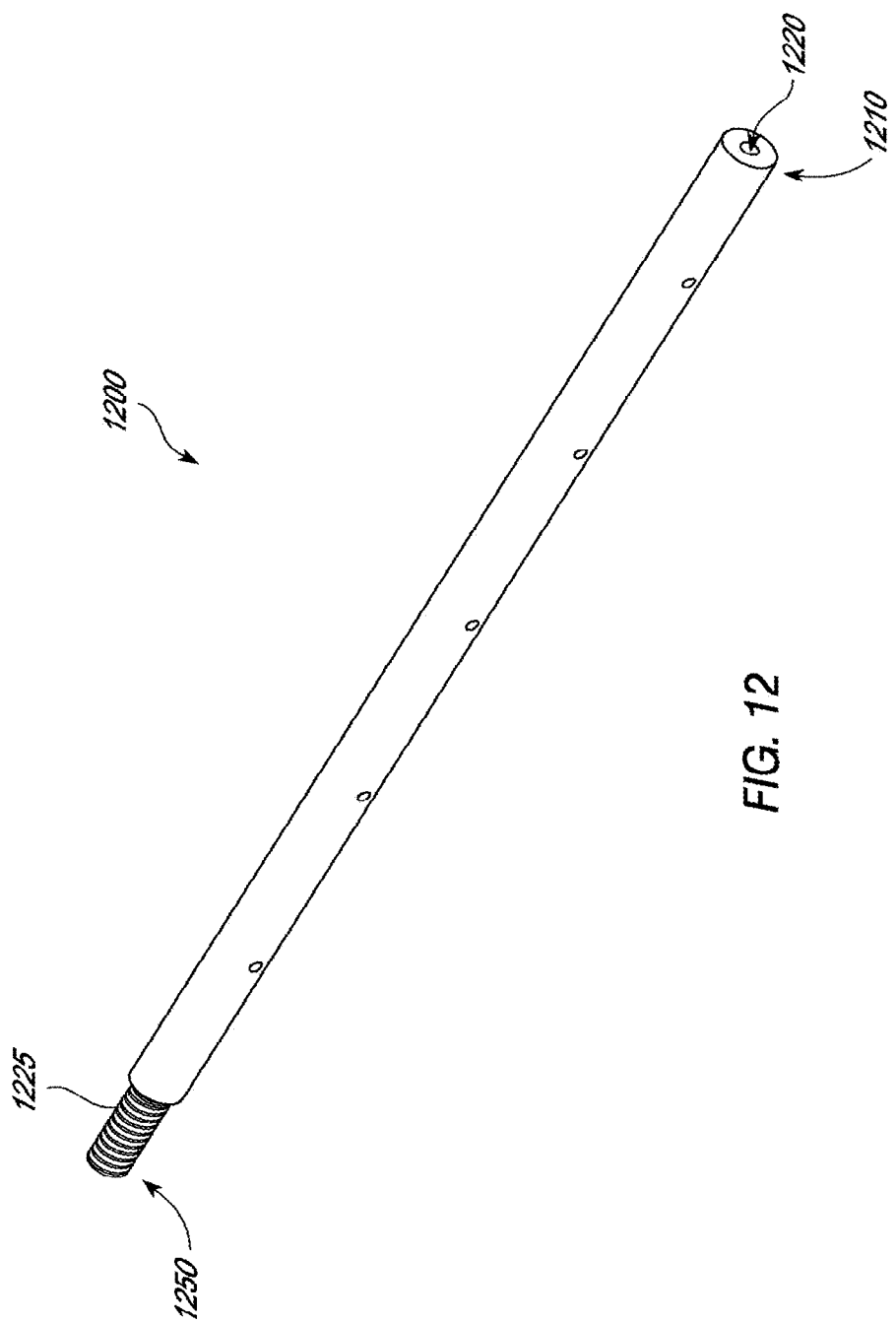
FIG. 12 is a perspective view of one embodiment of an outer rod.

FIG. 12 shows an embodiment of the outer tube 1200. The outer tube 1200 is attached at its proximal end 1205 to the distal end of handle via threading 1225. The distal end 1210 of the outer tube 1200 is configured such that the inner rod is drawn into the outer tube 1200 and through opening 1220 in the distal end 1210 of outer tube 1200 where it is secured to the expander. When the inner tube is advanced far enough that the expander locks into place or cannot advance anymore, the outer tube 1200 distal surface is surface-to-surface with the proximal surface of the anchor body. When the inner rod withdraws further into the outer tube upon the continued rotation of the deployment knob and advancement of the actuator shaft, the inner rod strips the threading from the expander and the inserter tool detaches from the anchor.

Figure 12A:
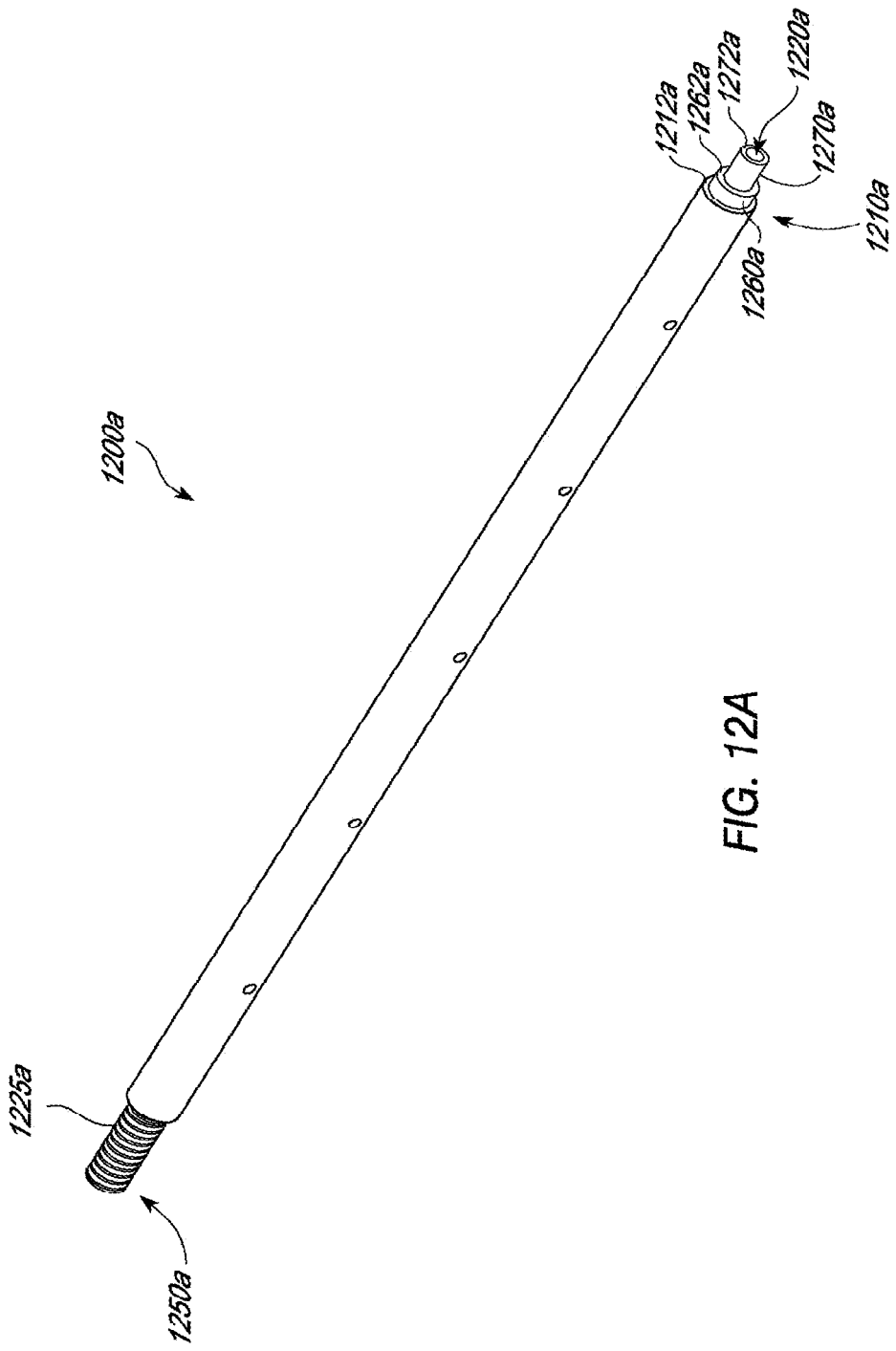
FIG. 12A is a perspective view of one embodiment of an outer rod configured for use with a two piece expander.

FIG. 12A shows an embodiment of the outer tube 1200*a* configured for use with a two piece expander. The outer tube 1200*a* is attached at its proximal end 1205*a* to the distal end of handle via threading 1225*a*. The distal end 1210*a* of the outer tube 1200*a* is configured such that the inner rod is drawn into the outer tube 1200*a* and through opening 1220*a* of the distal end 1210*a* of outer tube 1200*a* where it is secured to the expander. In some embodiments of an outer tube 1200*a* configured for use with a two piece expander, the distal end 1210*a* of the outer tube comprises a first abutment 1212*a*. In some embodiments, the first abutment 1212*a* is configured for abutting engagement with the second end 114, 414 of a dual expansion anchor 100, 400.

In some embodiments, the distal end 1210*a* of the outer tube 1200*a* comprises a first base 1260*a* and a first elevated abutment 1262*a*. In some embodiments, the first base 1260 is sized and dimensioned to fit within portions of the axial bore 116, 416 proximate to the second end 114, 414 of anchor 100, 400. The first base 1260*a* can be, for example, sized and shaped to slidably enter portions of the axial bore 116, 416 proximate to the second end 114, 414 of the dual expansion anchor 100, 400 when the dual expansion anchor 100, 400 is in its deployed or expanded configuration, or, alternatively, to slidably enter portions of the axial bore 116, 416 proximate to the second end 114, 414 of the dual expansion anchor 100, 400 when the dual expansion anchor 100, 400 is in its undeployed or unexpanded configuration. In some embodiments, the first elevated abutment 1262*a* of the outer tube 1200*a* is configured for abutting engagement with the second end 922 of the second expansion member 904.

In some embodiments, the distal end 1210*a* of the outer tube 1200*a* comprises a second base 1270*a* and a second elevated abutment 1272*a*. In some embodiments, the second base 1270*a* is sized and dimensioned to fit within portions of the axial bore 116, 416 proximate to the second end 114, 414 of anchor 100, 400. In some embodiments, second base 1270*a* is configured to slidingly extend through a thru-hole in the second expansion member 904. In some embodiments, the second base 1270*a* can be sized and configured to extend through the second expansion member 904. In some embodiments, the second base 1270*a* terminates at a point within the axial bore 116, 416 of the anchor 100, 400 where the second elevated abutment 1272*a* abuts the second end 912 of the first expansion member 902 when the dual expansion anchor is in its deployed or expanded configuration.

In some embodiments, the features of the distal end 1210*a* of the outer tube 1200*a* are configured to facilitate deployment of a dual expansion anchor 100, 400 with a two piece expander 900. In some embodiments, a dual expansion anchor 100, 400 can be positioned on the distal end 1210 of the outer tube 1200*a* of an inserter tool 1000*a*. Specifically, in some embodiments, the second expansion member 904 of a dual expansion anchor 100, 400 can abut the first elevated abutment 1262*a*. In some embodiments, the second base 1270*a* and the inner tube 1100*a* can extend through a thru-hole in the second expansion member 904 of a dual expansion anchor 900. In some embodiments, a second end 114, 414 of the anchor body 110, 410 can contact the second expansion member 904 of the two piece expander 900 and the first end 112, 412 of the dual expansion anchor 100, 400 can contact the first expansion member 902 of the two piece expander 900. In some embodiments the first expansion member 902 of the two piece expander 900 can be affixed to the inner tube 1100*a*. When the inner tube 1100*a* is longitudinally displaced to expand/deploy the anchor 100, 400, the inner tube 1100*a* applies a force to the first expansion member 902 of the two piece expander 900 while the first elevated abutment 1262*a* applies a reactionary force to the second expansion member 904 of the two piece expander 900. The application of these forces can displace the first and second expansion members 902, 904 of the two piece expander 900 until both the first and second expansion members 902, 904 of the two piece expander 900 are in their deployed position. More specifically, the first expansion member 902 of the two piece expander 900 can displace under applied forces until the first expansion member 902 of the two piece expander 900 contacts the second elevated abutment 1272*a*. Additionally, the second expansion member 902 of the two piece expander 900 can displace under the applied forces until second end 114, 414 of the anchor body 110, 410 contacts the first abutment 1212*a* of the distal end 1210*a* of the outer tube 1200*a*. In some embodiments, the second elevated abutment 1272*a* can be positioned relative to the first elevated abutment 1262*a*, and the dual expansion anchor 100, 400 can be designed such that the first expansion member 902 of the two piece expander 900 only contacts the second elevated abutment 1272*a* after the second end 114, 414 of the anchor body 110, 410 contacts the first abutment 1212*a* of distal end 1210*a* of the outer tube 1200*a*. After both the first and second expansion members 902, 904 of the two piece expander 900 reach their deployed/expanded positions, the inner tube 1100*a* is separated from the first expansion member 902 of the two piece expander 900, and the connection between the inserter tool 1000a and the anchor 100, 400 is terminated.

Figure 13B:
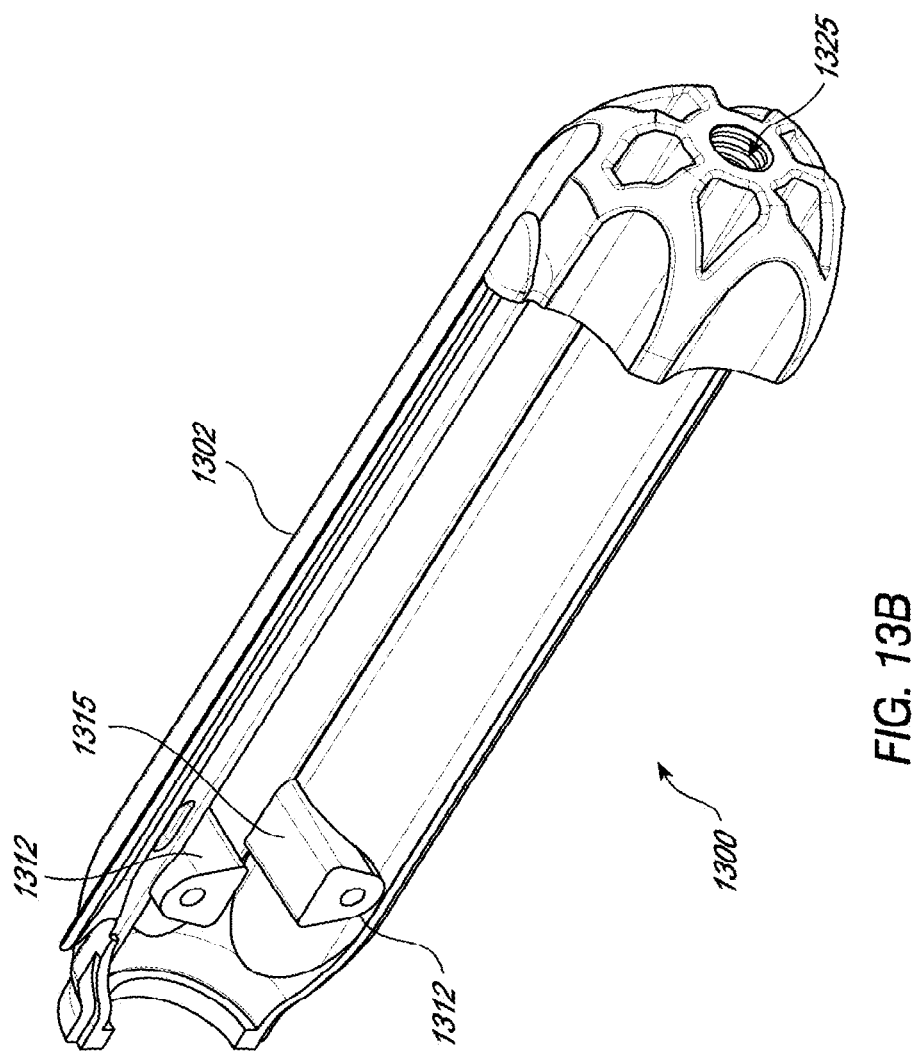
FIG. 13B is a perspective view of one embodiment of a portion of a handle body.

FIGS. 13A and 13B show embodiments of a handle body 1300. A handle body 1300 can comprise a handle piece 1302 and a lid piece 1304. FIG. 13A is a side view of a lid piece 1304 of the handle body 1300. The proximal end of the handle 1300 is configured to receive the deployment knob via the ridges 1330 which hold the knob secure. The actuator shaft is housed within the handle body 1300. A set of flat brackets or braces 1310 secure the actuator shaft within the handle 1300. The distal end of the handle 1300 is configured to receive the outer tube via threads at opening 1350. The outer tube is permanently affixed to the handle 1300 at its distal end.

FIG. 13B depicts a perspective view of one embodiment of the handle portion 1302 of a handle 1300. Handle portion 1302 includes a threaded hole for threading engagement with threading 1225 of the outer tube 1200. Handle portion 1302 depicted in FIG. 13B further includes brace receiving openings 1312. Handle portion 1302 additionally includes flat surfaces 1315.

Figure 14:
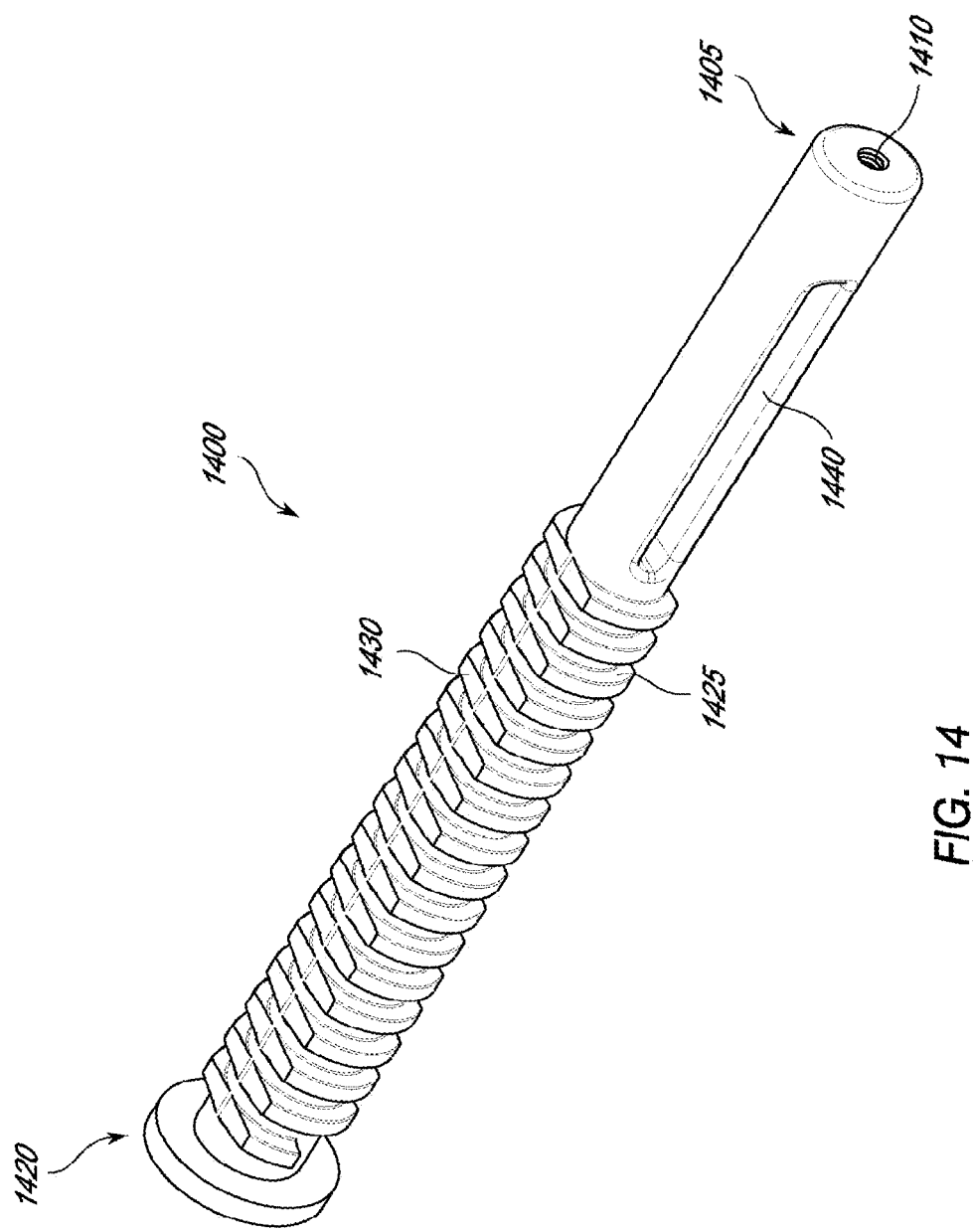
FIG. 14 is a perspective view of one embodiment of a threaded actuator shaft.

FIG. 14 depicts the threaded actuator shaft 1400. The actuator shaft 1400 is comprised of a distal end 1405 comprising a threaded hole 1410 which is configured to receive the inner rod 1100, a second threaded portion 1425 on the body of the shaft configured to advance the inner rod 1100, and a proximal end 1420 configured to secure within the deployment knob 1500. The threading 1425 of the actuator 1400 has two flat areas 1430, one on each side, where there is no threading. These flat areas 1430 fit within the flat surfaces 1315 of the handle 1300 such that the actuator 1400 cannot rotate within the handle.

The body of the actuator shaft 1400 is configured with threading 1425 to permit the shaft 1400 to advance the inner tube 1100. The body of the actuator shaft 1400 is not perfectly round, but rather is oval shaped with flat sides 1430 that are fit into the handle body 1300 in such a way that the actuator shaft 1400 cannot itself rotate when the deployment knob 1500 is turned and the shaft 1400 advances via knob 1500. Thus, the threads do not go all the way around the shaft but rather flatten out on the flattened sides of the shaft. The actuator shaft is configured as a coaxial system. That is, the expander, inner tube 1100 and actuator 1400 are configured to operate as one piece. The flat surfaces 1315 in the handle make the actuator shaft 1400 stay on plane such that the actuator shaft 1400 itself cannot rotate within the handle 1300. The proximal end of the inner tube 1100 couples with the distal end of the actuator shaft 1400 via threading.

Figure 15:
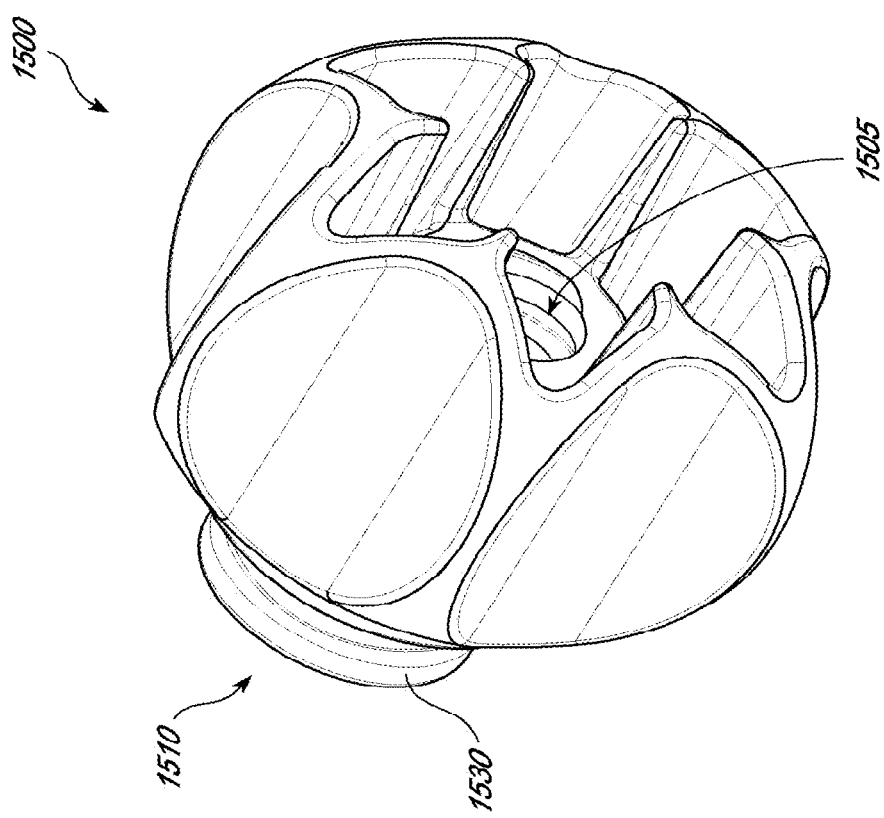
FIG. 15 is a perspective view of one embodiment of a deployment knob.

Moving to FIG. 15, a deployment knob 1500 is shown. The deployment knob 1500 comprises a central hole 1510 which is configured with threading 1505, and a groove 1530 configured to be received by a corresponding ridge 1330 of the handle 1300. The threading 1505 in the central hole 1510 is configured to receive the actuator shaft 1400. The deployment knob 1500 is configured to advance, relative to the deployment knob 1500, the inner rod 1100 via the actuator shaft 1400. The actuator shaft 1400 is joined at its proximal end to the distal end of the deployment knob 1500 via threading 1505 in the central hole 1510. The actuator shaft 1400 is attached to the inner rod 1100 by way of the proximal end of the inner rod 1100 advancing into the distal end of the actuator shaft via threading so that when the deployment knob 1500 is rotated, the mechanism of the shaft 1400 advances the inner rod 1100 proximally such that the expander is then advanced into the anchor body to expand the anchor body into bone and secure the anchor.

In one embodiment, the deployment knob 1500 is threaded 1505 to receive the actuator shaft via the groove 1530 of knob 1500 fitting with the proximal end ridge 1330 of the handle body 1300 As the deployment handle is turned, the actuator shaft 1400 is advanced in a proximal direction until the anchor body is deployed and locked into place.

Figure 16:
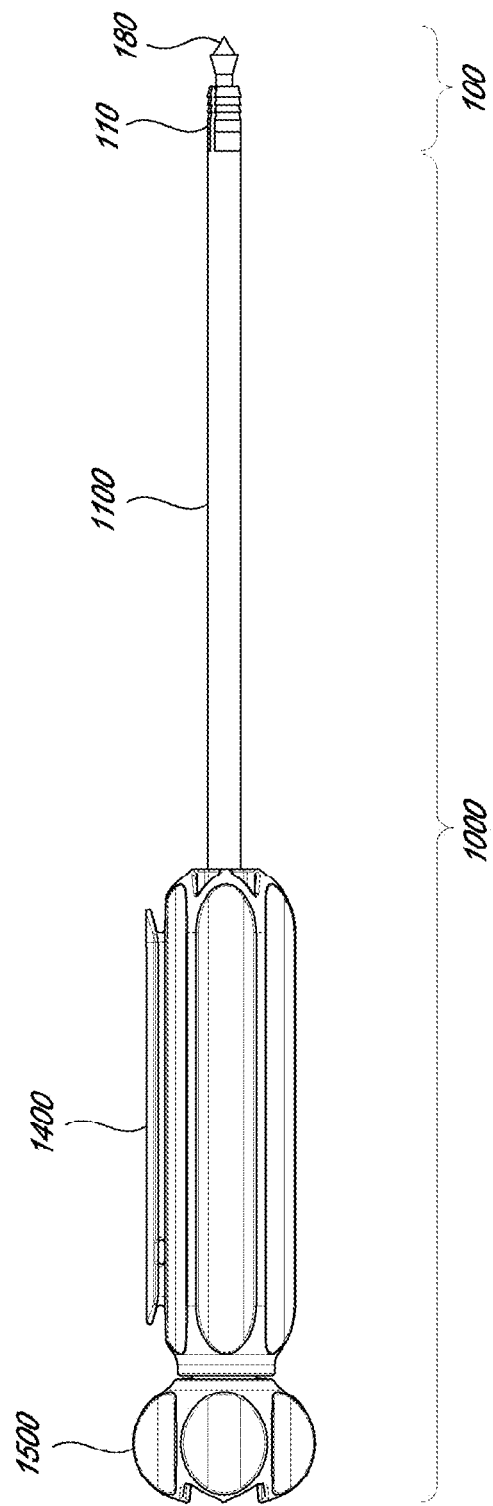
FIG. 16 depicts a side view of one embodiment of an inserter with an attached anchor.
Figure 17:
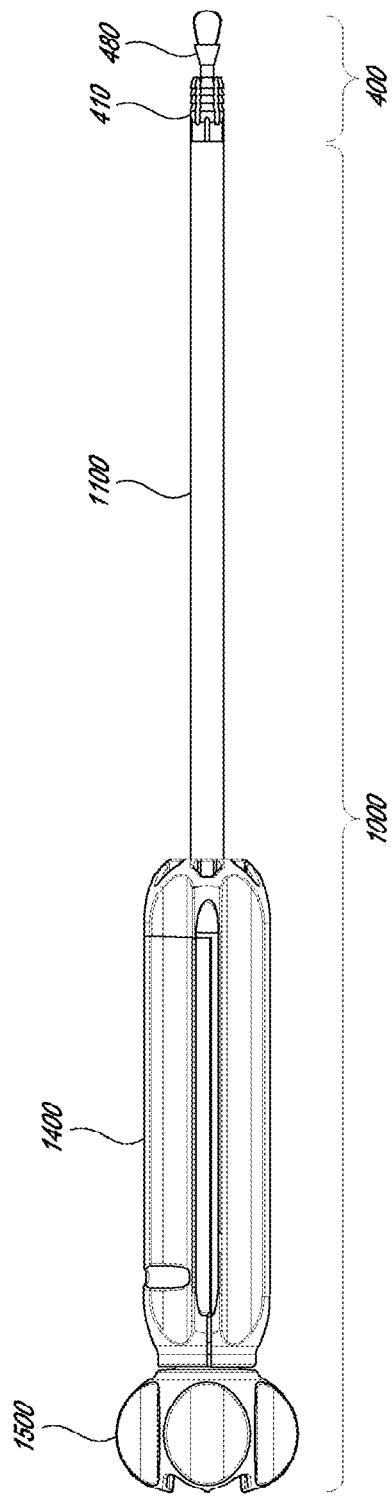
FIG. 17 depicts a side view of one embodiment of an inserter with an attached anchor.

FIG. 16 shows one embodiment of a dual expansion anchor 100 coupled to the inserter tool 1000 and FIG. 17 shows one embodiment of a dual expansion anchor 400 coupled to the inserter tool 1000. The anchors comprise the anchor body 110, 410 and the expander 180, 480. Expander 180 depicted in FIG. 16 includes a penetrating member 756 for securing the anchored material. Expander 480 as depicted in FIG. 17 includes a suture 761 passing through holes 766, 768 in the expander 480 and forming a loop 763 for securing the anchored material. A person of skill in the art will recognize that any of the above disclosed, or other features configured for engaging with and capturing material to be secured to the bone can be used in connection with a dual expansion anchor 100, 400 coupled to an inserter tool 1000.

The inserter tool 1000, as shown, includes the outer tube 1200, the handle 1300 and the deployment knob 1500. The inner rod 1100 is positioned within the outer tube 1200, and the outer tube is flush with the anchor body 110, 410. The outer tube 1200 may hold the anchor body 110, 410 steady during insertion and deployment. The inner rod 1100 extends through the anchor body 110, 410 and couples with the expander 180, 480 via threading. The expander 180, 480 is configured to be advanced through the distal end of the anchor body 110, 410 by the inner rod 1100 via a rotating the deployment knob 1500.

In another embodiment, the inner rod 1100 extends through the expander 180, 480. The inner rod 1100 is configured with a sharp, pointed tip such that the tip of the inner rod 1100 spears or captures tissue to secure into the bone hole before the anchor body 110, 410 is fully deployed.

The inner rod 1100 provides the mechanism to draw the expander 180, 480 into the central bore 116, 416 in the anchor body 110, 410 to fully expand the anchor body 110, 410. During deployment of the tissue capture anchor 100, 400, the inner rod 1100 is continually advanced via a screwing motion until the expander locks with the anchor body. As the deployment knob 1500 continues to turn and the inner rod 1100 continues to pull on the threads of the expander 180, 480, the inner rod 1100 strips the threads from the inside of the expander 180, 480 and the insertion tool 1000 releases from the anchor body 110, 410. Any thread shavings are contained within the outer tube 1200.

Figure 18:
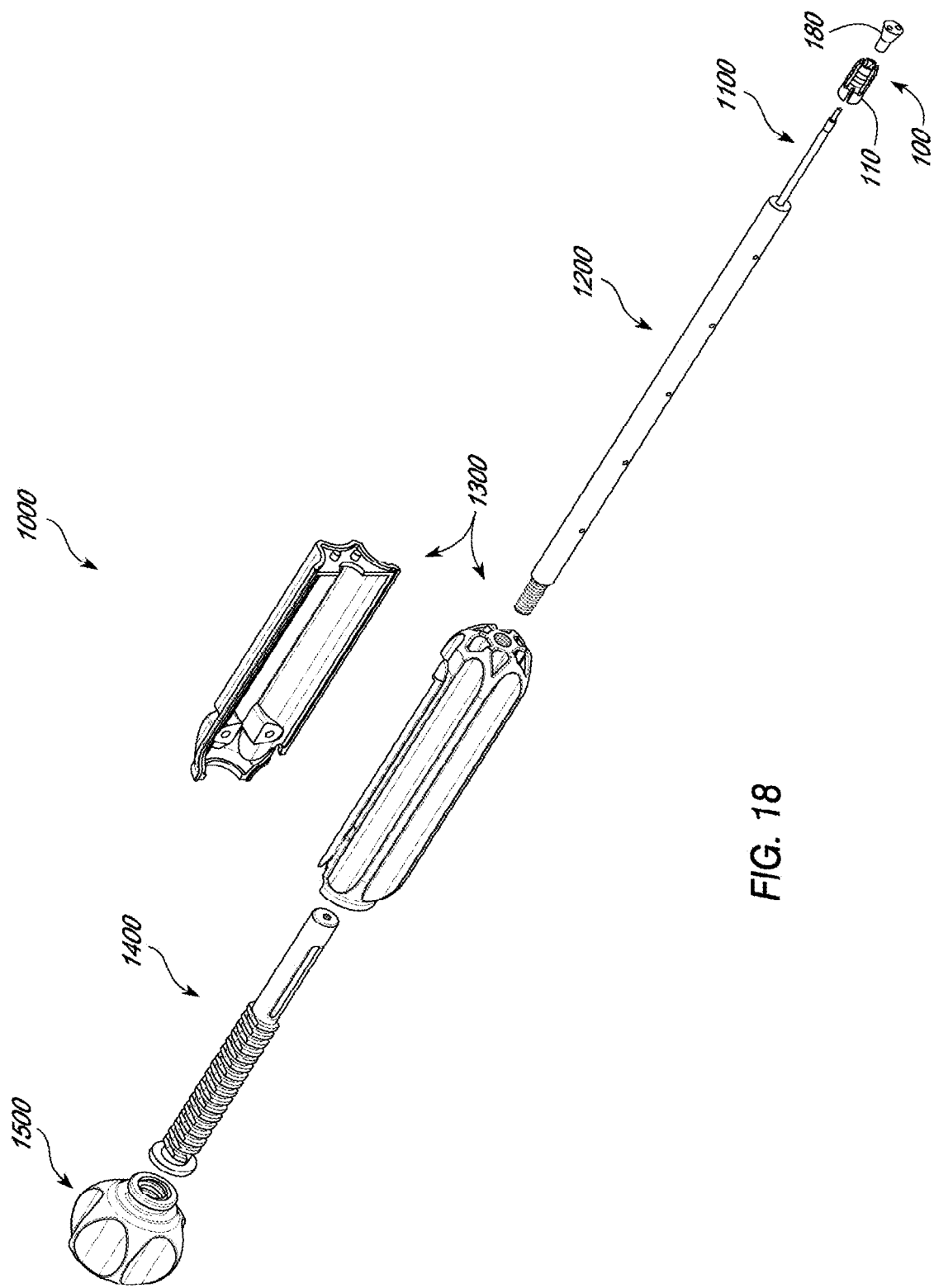
FIG. 18 depicts an exploded view of one embodiment of an inserter and anchor.

FIG. 18 illustrates an exploded view of the anchor 100 and the inserter 1000. The tissue capture anchor 100 comprises the anchor body 110 and the expander 180. The inserter tool 1000, as shown, includes the outer tube 1200, the handle 1300 and the deployment knob 1500. The inner rod 1100 is positioned within the outer tube 1200, and the outer tube is flush with the anchor body 110. The outer tube 1200 may hold the anchor body 110 steady during insertion and deployment. The inner rod 1100 extends through the anchor body 110 and couples with the expander 180 via threading. The expander 180 is configured to be advanced through the distal end of the anchor body 110 by the inner rod 1100 via a rotating the deployment knob 1500.

The inner rod 1100 provides the mechanism to draw the expander 180 into the central hole 116 in the anchor body 110 to fully expand the anchor body 110. During deployment of the tissue capture anchor 100, the inner rod 1100 is continually advanced via a screwing motion until the expander locks with the anchor body. As the deployment knob 1500 continues to turn and the inner rod 1100 continues to pull on the threads of the expander 180, the inner rod 1100 strips the threads from the inside of the expander 180 and the insertion tool 1000 releases from the anchor body 110. Any thread shavings are contained within the outer tube 1200.

In some embodiments, a pre-attached delivery handle is provided. In some embodiments, the insertion tool or delivery handle is disposable. In other embodiments, the insertion tool can be sterilized, reloaded and reused.

Those of skill in the art will appreciate other inserters and mechanisms that may be used to insert and deploy the dual expansion anchor 100, 400 described herein.

Although a particular inserter device for inserting and manipulating dual expansion anchor 100, 400 has been described, it should be understood that other inserter designs may be used for manipulating the parts of dual expansion anchor 100, 400 described above to insert the anchor into bone and tissue to the bone. For example, it may be possible to use separate tools for inserting the anchor and deploying the anchor.

It will be appreciated that there are numerous combinations of anchors and their placement that may be used to secure soft tissue to bone by the methods and devices described herein. These variations as well as variations in the design of the above described anchor devices and inserter devices are within the scope of the present disclosure.

Methods of Attaching Soft Tissue to Bone

Various embodiments include methods for attaching soft tissue to bone. In some embodiments, the methods include using the tissue capture anchors described above. In one preferred embodiment, a biceps tenodesis procedure is performed arthroscopically.

The biceps tendon connects the biceps muscle to the bone. The biceps tendon connects the biceps muscle to the bone. The tendon passes from the muscle to the shoulder joint. Biceps tendon problems can also occur in conjunction with a rotator cuff tear.

A biceps tenodesis is a procedure that cuts the normal attachment of the biceps tendon on the shoulder socket and reattaches the tendon to the bone of the humerus (arm bone). By performing a biceps tenodesis, the pressure of the biceps attachment is taken off the cartilage rim of the shoulder socket (the labrum), and a portion of the biceps tendon can be surgically removed. Essentially a biceps tenodesis moves the attachment of the biceps tendon to a position that is out of the way of the shoulder joint.

A biceps tenodesis is often, but not always, performed in patients with significant biceps tendon symptoms, and evidence at the time of viewing of biceps tendon inflammation or tears.

The procedure using a tissue capture anchor described herein merely requires drilling the bone hole and capturing the tendon with the anchor and dragging the tendon into the bone hole. In some embodiments, a further advantage when using an awl to make the bone hole is that the whole procedure can be percutaneous.

Figure 19:
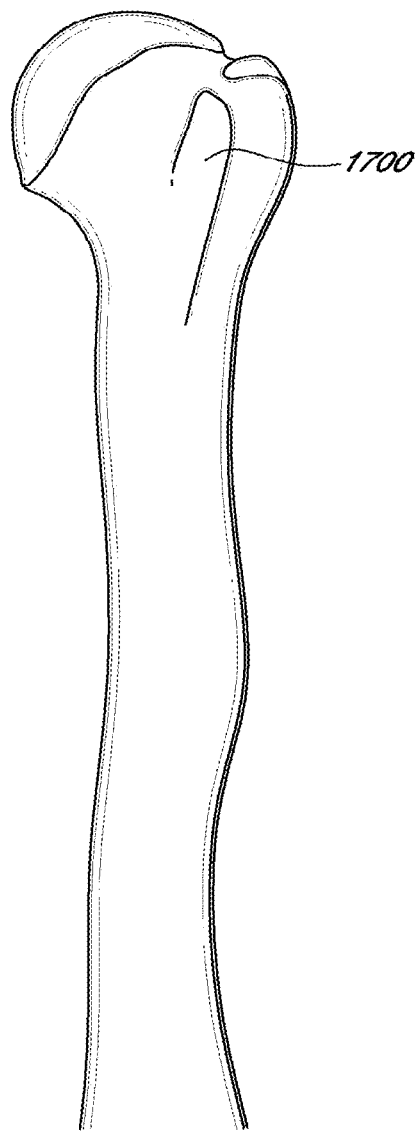
FIG. 19 depicts a bicipital groove and surrounding bone of the shoulder and biceps.
Figure 20:
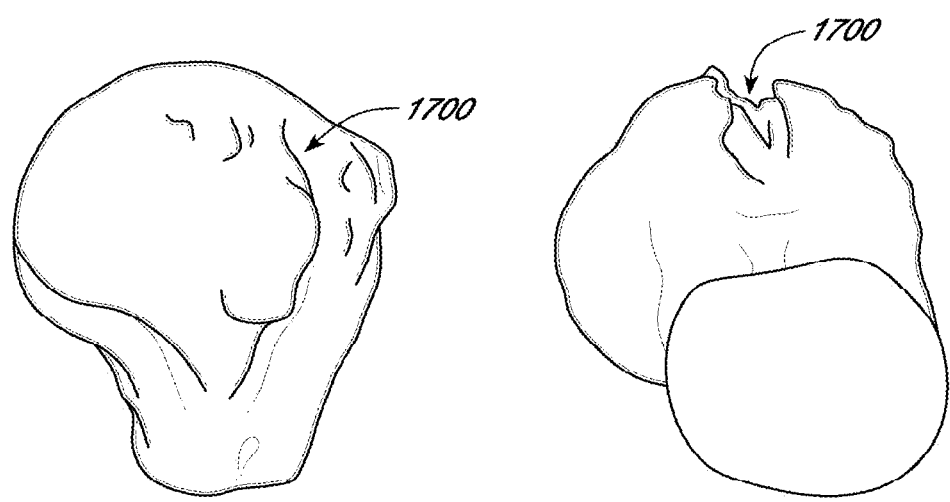
FIG. 20 depicts a bicipital groove and surrounding bone of the shoulder and biceps.

In one method, the procedure is performed arthroscopically. In one embodiment, the procedure is performed non-arthroscopically. In one embodiment, for example, a percutaneous approach may be used. In one embodiment, a 6 mm anchor is used, although different sizes and materials may be used. In some instances the hole into which the tissue capture anchor will be inserted is made by making a clearance hole for the anchor in the superior portion of the bicipital groove 1700, as shown in FIG. 19, using a drill bit or suitably sized awl. The hole may also be made in any other suitable position depending on pathology of the tendon, etc. FIGS. 19 and 20 show different views of the bicipital groove and surrounding bone of the shoulder and biceps. The bicipital groove is a furrow on the upper part of the humerus occupied by the long head of the biceps and is also called the intertubercular groove. In some embodiments a 7 mm drill bit is used; however in other embodiments, a different sized drill bit can be used. In one embodiment, the clearance hole can range from 5 mm wide to 9 mm wide, from 6.5 mm to 8 mm wide, or any other desired range. In other embodiments, the size of the clearance hole will vary, as the size depends on the size of the anchor. Depending on the softness of the bone and the size of the anchor, the hole can be from 8 mm-40 mm deep, approximately 21 mm deep, approximately 30 mm deep, or any other desired depth. For example, in one embodiment, a 6 mm tissue capture anchor is used, and for soft bone, the hole can be at least 11 mm deep. For average bone, the hole can be approximately 10-12 mm deep. For very soft bone, the hole can be approximately 20 mm.

Figure 21:
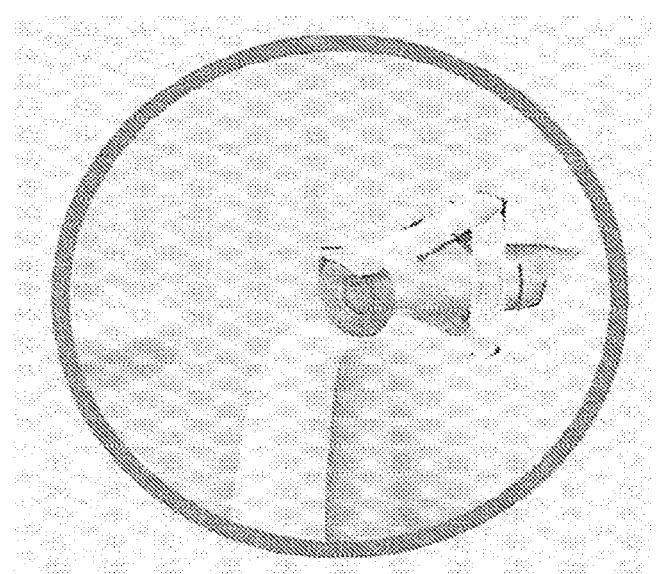
FIG. 21 depicts a tendon held in a hole by an anchor.
Figure 22:
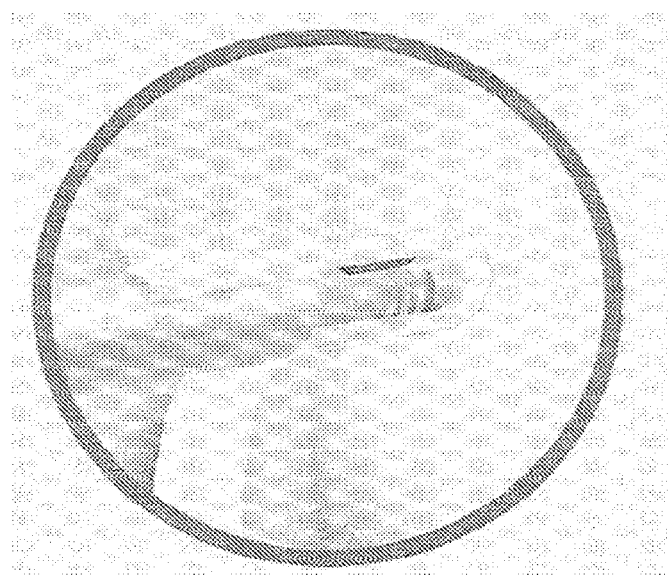
FIG. 22 depicts the insertion of a tendon and anchor into a hole.
Figure 23:
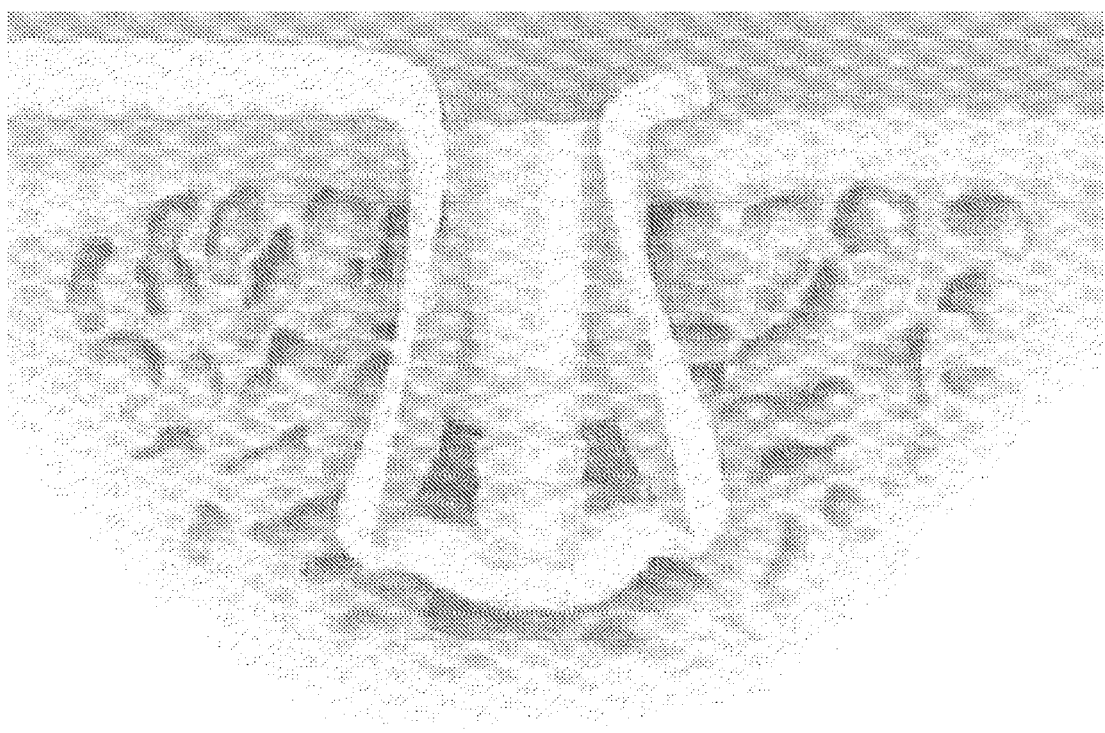
FIG. 23 depicts the side view of a deployed anchor securing a tendon in a hole.

The implantation site is cleared of any soft tissue in the region of the bone hole using a bur or other suitable means. Angled protrusions or teeth may be used that provide greater resistance to removal of the anchor body 110, 410 than to insertion. As shown in FIG. 21, the tendon will then be captured by the anchor and forced into the clearance hole and the anchor deployed as shown in FIG. 22. As shown in FIG. 23, the tendon is essentially folded around the anchor longitudinally resulting in a double surface contact. As described above, the tendon may be captured using a variety of methods including those associated with the different expander types of FIG. 7A.

In one nonlimiting embodiment, the shoulder preparation is as that used by Richards and Brukhart ("A Biomechanical Analysis of Two Biceps Tenodesis Fixation Techniques" Arthroscopy. The Journal OF Arthroscopic and Related Surgery Vol 21, No 7 (July), 2005: pp 861-866) which is incorporated by herein by reference in its entirety. The shoulder will undergo soft tissue dissection to the level of the rotator cuff. At this point, the surpraspinatus tendon insertion is reflected by sharp dissection and the long head biceps tendon inspected for any evidence of pathology. The tendon of the LHB is then sharply incised, freeing from its intra-articular origin at the superior aspect of the glenoid as well as dividing it as the musculotendinous junction so that the biceps tendon is a free segment. In other embodiments, other methods of shoulder preparation are used.

In some exemplary embodiments, repairs are complete by drilling a clearance hole for the anchor in the superior portion of the bicipital groove using a standard drill bit. As shown in FIGS. 21-23, the tendon will then be captured by the anchor and forced in to the clearance hole and the anchor placed to capture the tendon. The tendon will be essentially folded around the anchor longitudinally, resulting in a double surface contact. The proximal surface of the anchor will be situated flush with the cortical surface. In some embodiments, the hole can be located in other portions of the bone. In one exemplary embodiment, the hole may be placed, approximately, I cm distal to the end of the bicipital groove.

In another embodiment, anchors as described above are used for anterior cruciate ligament (ACL) repair. In this embodiment, a femoral tunnel is drilled in the bone. One or two bundles of hamstring tendon are captured by the anchor. The anchor is then inserted into the bone and deployed as discussed above. As described above, the tendon may be captured using a variety of methods including those associated with the different expander types of FIG. 7A.

In one embodiment, a hole is drilled in to the bone at a diameter of about 9 mm. The anchor is positioned such that a grasper tool can be implemented to grasp a tendon secure the tendon. The tendon can then be manipulated and moved or positioned. In one embodiment, a double bundle of tendons is inserted into a single bone tunnel in the femur. In one embodiment, a gracilis and a semitendinosus tendon are both doubled over for insertion into the bone hole. The anchor, which, in one embodiment may be about 8 mm or 9 mm in diameter, is inserted into the bone hole with the doubled over tendons. Due to the size of the hole, the anchor, which may be 8 or 9 mm in diameter is inserted with the doubled over tendons draped over its tip into the hole. The anchor is also suited for single bundle single tunnel and single bundle double tunnel procedures. In other embodiments, the bone hole and the anchor can be difference sizes as needed.

In one embodiment, the surgeon drills through the tibia and up into the femur and loads the anchor plus tendons through the tibial tunnel. In one embodiment, an anteromedial portal is used to drill the femoral tunnel and a separate tibial tunnel.

It will be appreciated by those of skill in the art that the tissue capture anchor 100, 400 and inserter tool 1000 provide a system for easy attachment of a tendon or tissue to bone. The anchor 100, 400 may be inserted into bone with minimal disruption of surrounding tissue. Only an access route having the diameter of the outer tube 1200 and the anchor body 110, 410 is required. Furthermore, the anchor can be securely attached to the bone without having to insert additional instrumentation into the site or without performing any cumbersome attachment maneuvers such as knot tying.

In another embodiment, anchors as described above are used for other procedures in the knee such as, for example, patellofemoral ligament reconstruction, posterolateral corner reconstruction, and tibial anchor back-up for an ACL procedure.

In some embodiments, anchors as described above can be used for numerous tissue fixation procedures in foot and ankle. These include flexor hallucis longus transfer to Achilles for loss of Achilles mechanism; posterior tibial tendon to anterior midfoot (middle cuneiform) also known as bridle/modified bridle procedure for foot drop; Lateral ligament reconstruction with allograft (potentially as primary with Brostrom-Gould type procedure) for ankle instability or non-anatomic lateral ligament reconstruction using split peroneus *brevis*; deltoid ligament reconstruction with allograft (for deltoid insufficiency); flexor digitorum longus or flexor hallucis longus transfer to peroneal for non-reconstructable peroneal tendon tears and reconstruction of torn tibialis anterior with extensor hallucis longus tendon transfer.

Although the invention has been described with reference to embodiments and examples, it should be understood that numerous and various modifications can be made without departing from the spirit of the invention. Accordingly, the invention is limited only by the following claims.

What is claimed is:

1. A bone anchor system, comprising:
   a bone anchor inserter having a proximal end and a distal end, the bone anchor inserter comprising:
      a handle;
      a distal shaft connected to the handle;
      an anchor body connected to the distal shaft; and
      an actuator positioned on the proximal end that is configured to move an expander from a first position to a second position; and
   a bone engaging member having a first end and a second end, the bone engaging member comprising:
      a first plurality of bone-engaging tines extending longitudinally toward the first end;
      a second plurality of bone-engaging tines extending longitudinally toward the second end;
   the expander comprising a first portion and a second portion positioned along a central longitudinal axis;
   wherein the expander is positioned between the first plurality of bone engaging tines when the expander is in a first position,
   wherein the expander is positioned between the first plurality of bone engaging tines and between the second plurality of bone engaging tines when the expander is in a second position; and
   wherein the expander is configured to expand both the first plurality of tines and the second plurality of tines outward upon movement of the expander relative to the bone-engaging member from the first position to the second position.

2. The bone anchor system of claim 1, wherein the first plurality of bone engaging tines are equiangularly positioned around a longitudinal axis of the bone engaging member.

3. The bone anchor system of claim 1, wherein the second plurality of bone engaging tines are equiangularly positioned around a longitudinal axis of the bone engaging member.

4. The bone anchor system of claim 1, wherein the first portion of the expander is configured to radially expand the first plurality of tines when the expander is moved from the first position to the second position.

5. The bone anchor system of claim 1, wherein the second portion of the expander is configured to radially expand the second plurality of tines when the expander is moved from the first position to the second position.

6. The bone anchor system of claim 1, wherein the expander is configured to expand both the first plurality of tines and the second plurality of tines outward upon the proximal movement of the expander.

* * * * *